US010544168B2

(12) United States Patent
Beard et al.

(10) Patent No.: US 10,544,168 B2
(45) Date of Patent: Jan. 28, 2020

(54) LIGAND-EXCHANGEABLE NANOPARTICLES AND METHODS OF MAKING THE SAME

(71) Applicants: Alliance for Sustainable Energy, LLC, Golden, CO (US); Colorado School of Mines, Golden, CO (US); The Regents of the university of Colorado, a body corporate, Denver, CO (US)

(72) Inventors: Matthew C. Beard, Arvada, CO (US); Daniel McCray Kroupa, Denver, CO (US); Alan Sellinger, Golden, CO (US)

(73) Assignees: Alliance for Sustainable Energy, LLC, Golden, CO (US); Colorado School of Mines, Golden, CO (US); The Regents of the University of Colorado, a body corporate, Denver, CO (US)

( * ) Notice: Subject to any disclaimer, the term of this patent is extended or adjusted under 35 U.S.C. 154(b) by 304 days.

(21) Appl. No.: 15/623,910

(22) Filed: Jun. 15, 2017

(65) Prior Publication Data

US 2017/0362255 A1 Dec. 21, 2017

Related U.S. Application Data

(60) Provisional application No. 62/350,245, filed on Jun. 15, 2016.

(51) Int. Cl.
*C07F 7/00* (2006.01)
*C09K 11/06* (2006.01)
*C09D 11/50* (2014.01)

(52) U.S. Cl.
CPC .............. *C07F 7/003* (2013.01); *C09D 11/50* (2013.01); *C09K 11/06* (2013.01); *C09K 2211/1007* (2013.01); *C09K 2211/188* (2013.01)

(58) Field of Classification Search
CPC ........ C09D 11/03; C09K 11/06; C09K 11/661
See application file for complete search history.

(56) References Cited

U.S. PATENT DOCUMENTS

| | | | |
|---|---|---|---|
| 7,199,393 B2 * | 4/2007 | Park | B82Y 20/00 257/40 |
| 7,517,718 B2 | 4/2009 | Mitzi et al. | |
| 7,700,200 B2 | 4/2010 | Bulovic et al. | |
| 8,093,494 B2 | 1/2012 | Gur et al. | |
| 8,765,014 B2 | 7/2014 | Cho et al. | |
| 8,876,272 B2 * | 11/2014 | Linton | C09D 11/326 347/100 |
| 9,093,656 B2 | 7/2015 | Pan et al. | |
| 2006/0018835 A1 * | 1/2006 | Lucien Malenfant | A61K 49/1848 424/9.3 |
| 2008/0014463 A1 | 1/2008 | Varadarajan et al. | |
| 2015/0083970 A1 * | 3/2015 | Koh | C09K 11/02 252/301.35 |
| 2015/0329359 A1 * | 11/2015 | Santiago Berrios | C01B 19/007 423/509 |
| 2016/0133463 A1 | 5/2016 | Luther et al. | |

FOREIGN PATENT DOCUMENTS

WO WO 2016/020939 * 2/2016

OTHER PUBLICATIONS

Giansante et al, "Colloidal Arenethiolate-Capped PbS Quantum Dots: Optoelectronic Properties, Self-Assembly, and Application in Solution-Cast Photovoltaics", Journal of Physical Chemistry C, 117, May 2013, pp. 13305-13317.*
Giansante et al, ""Darker-than-Black" PbS Quantum Dots: Enhancing Optical Absorption of Colloidal Semiconductor Nanocrystalsvia Short Conjugated Ligands", Journal of the Americal Chemical Society, 137, Jan. 9, 2015, pp. 1875-1886.*
Song, J. et al., "Quantum Dot Light-Emitting Diodes Based on Inorganic Perovskite Cesium Lead Halides ($CsPbX_3$)," Advanced Materials, vol. 27, 2015, pp. 7162-7167.
Swarnkar, A. et al., "Quantum dot-induced phase stabilization of $\alpha$-$CsPbI3$ perovskite for high-efficiency photovoltaics," Science, vol. 354, Issue 6308, Oct. 7, 2016, pp. 92-95.
International Search Report from corresponding PCT patent application, PCT/US17/35156, dated Sep. 1, 2017, 3 pages.
Written Opinion of the International Searching Authority from corresponding PCT patent application, PCT/US17/35156, dated Sep. 1, 2017, 7 pages.
Anderson, N. et al., "Ligand Exchange and the Stoichiometry of Metal Chalcogenide Nanocrystals: Spectroscopic Observation of Facile Metal-Carboxylate Displacement and Binding," Journal of the American Chemical Society, vol. 135, 2013, pp. 18536-18548.
Beal, R. et al., "Cesium Lead Halide Perovskites with Improved Stability for Tandem Solar Cells," Journal of Physical Chemistry Letters, vol. 7, 2016, pp. 746-751.
Boles, M. et al., "The surface science of nanocrystals," Nature Materials, vol. 15, Feb. 2016, pp. 141-153.
Brown, P. et al., "Energy Level Modification in Lead Sulfide Quantum Dot Thin Films through Ligand Exchange," ACS Nano, vol. 8, No. 6, pp. 5863-5872.
Brus, L., "Electron-electron and electron-hole interactions in small semiconductor crystallites: The size dependence of the lowest excited electronic state," Journal of Chemical Physics, vol. 80, No. 9, May 1, 1984, pp. 4403-4409.
Carey, G. et al., "Colloidal Quantum Dot Solar Cells," Chemical Reviews, vol. 115, 2015, pp. 12732-12763.
Chuang, C. et al., "Improved performance and stability in quantum dot solar cells through band alignment engineering," Nature Materials, vol. 13, No. 8, Aug. 2014, pp. 1-13.

(Continued)

*Primary Examiner* — C Melissa Koslow
(74) *Attorney, Agent, or Firm* — Michael A. McIntyre

(57) ABSTRACT

An aspect of the present disclosure is a nanocrystal that includes a nanocrystal core and a ligand coordinated to a surface of the nanocrystal core, where the ligand includes a functionalized aromatic molecule. In some embodiments of the present disclosure, the functionalized aromatic molecule may include at least one of cinnamic acid (CAH) and/or a functionalized CAH molecule.

19 Claims, 22 Drawing Sheets

(56) References Cited

OTHER PUBLICATIONS

Crisp, R. et al., "Metal Halide Solid-State Surface Treatment for High Efficiency PbS and PbSe QD Solar Cells," Scientific Reports, 5:9945, Apr. 24, 2015, pp. 1-6.

Dastidar, S. et al., "High Chloride Doping Levels Stabilize the Perovskite Phase of Cesium Lead Iodide," ACS NanoLetters, vol. 16, May 2, 2016, pp. 3563-3570.

Debnath, R. et al., "Solution-processed colloidal quantum dot photovoltaics: A perspective," Energy & Environmental Science, vol. 4, 2011, pp. 4870-4811.

Eperon, G. et al., "Inorganic caesium lead iodide perovskite solar cells," Journal of Materials Chemistry A, vol. 3, 2015, pp. 19688-1969.

Evans, C. et al., "Review of the synthesis and properties of colloidal quantum dots: the evolving role of coordinating surface ligands," Journal of Coordination Chemistry, vol. 65, No. 13, Jul. 10, 2012, pp. 2391-2414.

Fafarman, A. et al., "Thiocyanate-Capped Nanocrystal Colloids: Vibrational Reporter of Surface Chemistry and Solution-Based Route to Enhanced Coupling in Nanocrystal Solids," Journal of the American Chemical Society, vol. 133, 2011, pp. 15753-15761.

Frecker, T. et al., "Review-Quantum Dots and Their Application in Lighting, Displays, and Biology," ECS Journal of Solid State Science and Technology, vol. 5, No. 1, 2016, pp. R3019-R3031.

Frederick, M. et al., "Relaxation of Exciton Confinement in CdSe Quantum Dots by Modification with a Conjugated Dithiocarbamate Ligand," ACS Nano, vol. 4, No. 6, pp. 3195-3200.

Giansante, C. et al., "Colloidal Arenethiolate-Capped PbS Quantum Dots: Optoelectronic Properties, Self-Assembly, and Application in Solution-Cast Photovoltaics," Journal of Physical Chemistry, vol. 117, 2013, pp. 13305-13317.

Giansante, C. et al., "'Darker-than-Black' PbS Quantum Dots: Enhancing Optical Absorption of Colloidal Semiconductor Nanocrystals via Short Conjugated Ligands," Journal of the American Chemical Society, vol. 137, 2015, pp. 1875-1886.

Hansch, C. et al., "A Survey of Hammett Substituent Constants and Resonance and Field Parameters," Chemistry Reviews, vol. 91, 1991, pp. 165-195.

Hendricks, M. et al., "A tunable library of substituted thiourea precursors to metal sulfide nanocrystals," Science, vol. 348, Issue 6240, Jun. 12, 2015, pp. 1226-1230.

Jellicoe, T. et al., "Synthesis and Optical Properties of Lead-Free Cesium Tin Halide Perovskite Nanocrystals," Journal of the American Chemical Society, vol. 138, 2016, pp. 2941-2944.

Kovalenko, M. et al., "Colloidal Nanocrystals with Molecular Metal Chalcogenide Surface Ligands," Science, vol. 324, Jun. 12, 2009, pp. 1417-1420.

Lattante, S., "Electron and Hole Transport Layers: Their Use in Inverted Bulk Heterojunction Polymer Solar Cells," Electronics, vol. 3, 2014, pp. 132-164.

Liu, M. et al., "Double-Sided Junctions Enable High-Performance Colloidal-Quantum-Dot Photovoltaics," Advanced Materials, vol. 28, 2016, pp. 4142-4148.

Luther, J. et al., "Multiple Exciton Generation in Films of Electronically Coupled PbSe Quantum Dots," Nano Letters, vol. 7, No. 6, 2007, pp. 1779-1784.

Miller, E. et al., "Revisiting the Valence and Conduction Band Size Dependence of PbS Quantum Dot Thin Films," ACS Nano, vol. 10, 2016, pp. 3302-3311.

Moreels, I. et al., "Composition and Size-Dependent Extinction Coefficient of Colloidal PbSe Quantum Dots," Chemical Materials, vol. 19, Nov. 15, 2007, pp. 6101-6106.

Oh, S. et al., "Stoichiometric Control of Lead Chalcogenide Nanocrystal Solids to Enhance Their Electronic and Optoelectronic Device Performance," ACS Nano, vol. 7, No. 3, 2013, pp. 2413-2421.

Owen, J., The coordination chemistry of nanocrystal surfaces,: Science, vol. 347, Issue 6222, Feb. 6, 2015, pp. 615-616.

Palazon, F. et al., "Polymer-Free Films of Inorganic Halide Perovskite Nanocrystals as UV-to-White Color-Conversion Layers in LEDs," Chemistry of Materials, vol. 28, 2016, pp. 2902-2906.

Peterson, M. et al., "The Role of Ligands in Determining the Exciton Relaxation Dynamics in Semiconductor Quantum Dots," Annual Review of Physical Chemistry, vol. 65, 2014, pp. 317-339.

Protesescu, L. et al., "Nanocrystals of Cesium Lead Halide Perovskites ($CsPbX_3$, X=Cl, Br, and I): Novel Optoelectronic Materials Showing Bright Emission with Wide Color Gamut," NanoLetters, vol. 15, 2015, pp. 3692-3696.

Reinhart, C. et al., "Colloidally Prepared 3-Mercaptopropionic Acid Capped Lead Sulfide Quantum Dots," Chemistry of Materials, vol. 27, 2015, pp. 7313-7320.

Ripolles, T. et al., "Efficiency enhancement by changing perovskite crystal phase and adding a charge extraction interlayer in organic amine free-perovskite solar cells based on cesium," Solar Energy Materials & Solar Cells, vol. 144, 2016, pp. 532-536.

Santra, P. et al., "Improving Performance in Colloidal Quantum Dot Solar Cells by Tuning Band Alignment through Surface Dipole Moments," Journal of Physical Chemistry, vol. 119, 2015, pp. 2996-3005.

Smith, A. et al., "Effect of Ligand Structure on the Optical and Electronic Properties of Nanocrystalline PbSe Films," Journal of Physical Chemistry, vol. 116, 2012, pp. 6031-6037.

Sun, S. et al., "Ligand-Mediated Synthesis of Shape-Controlled Cesium Lead Halide Perovskite Nanocrystals via Reprecipitation Process at Room Temperature," ACS Nano, vol. 10, 2016, pp. 3648-3657.

Sutton, R. et al., "Bandgap-Tunable Cesium Lead Halide Perovskites with High Thermal Stability for Efficient Solar Cells," Materials Views, vol. 6, 2016, 1502458, 6 pages.

Talapin, D. et al., "PbSe Nanocrystal Solids for n- and p-Channel Thin Film Field-Effect Transistors," Science, vol. 310, Oct. 7, 2005, pp. 86-89.

Valizadeh, A., "Quantum dots: synthesis, bioapplications, and toxicity," Nanoscale Research Letters, vol. 7:480, 2012, 14 pages.

Yang, S. et al., "Tuning Semiconductor Band Edge Energies for Solar Photocatalysis via Surface Ligand Passivation," Nano Letters, vol. 12, 2012, pp. 383-388.

Zarghami, M. et al., "p-Type PbSe and PbS Quantum Dot Solids Prepared with Short-Chain Acids and Diacids," ACS Nano, vol. 4, No. 4, 2010, pp. 2475-2485.

Kulbak, M. et al., "How Important Is the Organic Part of Lead Halide Perovskite Photovoltaic Cells? Efficient $CsPbBr3$ Cells," Journal of Physical Chemistry Letters, vol. 6, 2015, pp. 2452-2456.

\* cited by examiner

LIGAND-EXCHANGEABLE NANOPARTICLES AND METHODS OF MAKING THE SAME

CROSS-REFERENCE TO RELATED APPLICATIONS

This application claims the benefit of U.S. Provisional Application No. 62/350,245 filed Jun. 15, 2016, the contents of which are incorporated herein by reference in their entirety.

CONTRACTUAL ORIGIN

The United States Government has rights in this disclosure under Contract No. DE-AC36-08GO28308 between the United States Department of Energy and the Alliance for Sustainable Energy, LLC, the Manager and Operator of the National Renewable Energy Laboratory.

BACKGROUND

Colloidal semiconductor nanocrystals, or quantum dots (nanocrystals), have been an active area of research in numerous scientific disciplines due to their highly tunable optical and electronic properties. Since their initial discovery, researchers have used quantum confinement to easily tune nanocrystal band gaps throughout the visible and near infrared spectrum by varying the nanocrystal core material and diameter. Subsequently, researchers have found that surface chemistry also plays a vital role in emergent nanocrystal optical and electronic properties due to large nanocrystal surface to volume ratios at nanoscale sizes. Researchers have also pursued post synthetic surface chemistry modification, or ligand exchange, as another avenue of tailoring nanocrystals to make nanocrystal-ligand material systems with significantly diverse optical and electronic properties significantly unlike those of the starting nanocrystal-ligand system.

SUMMARY

An aspect of the present disclosure is a nanocrystal that includes a nanocrystal core and a ligand coordinated to a surface of the nanocrystal core, where the ligand includes a functionalized aromatic molecule. In some embodiments of the present disclosure, the functionalized aromatic molecule may include at least one of cinnamic acid (CAH) and/or a functionalized CAH molecule.

In some embodiments of the present disclosure, the functionalized CAH molecule may include at least one of cinnamic acid, 2,3,4,5,6-pentafluorocinnamic acid, 3,5-bis (trifluoromethyl)cinnamic acid, 4-(2,2-dicyanovinyl)cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tertbutylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, and/or 3,4-(2,5-pyrrolidinedione)cinnamic acid In some embodiments of the present disclosure, the functionalized aromatic molecule may include at least one of styrylphosphonic acid, 4-formylstyrylphosphonic acid, (4-(2,2-dicyanovinyl)styryl)phosphonic acid, 2,6-difluorostyrylphosphonic acid, 4-trifluoromethylstyrylphosphonic acid, 4-methoxystyrylphosphonic acid, 3-methylstyrylphosphonic acid, benzoic acid, 4-methylbenzoic acid, 4-mercaptobenzoic acid, 4-methoxybenzoic acid, 4-fluorobenzoic acid, 4-hydroxybenzoic acid, 4-nitrobenzoic acid, 4-cyanobenzoic acid, 4-formylbenzoic acid, 4-trifluoromethylbenzoic acid, 4-chlorobenzoic acid, 4-bromobenzoic acid, 4-iodobenzoic acid, 4-fluorobenzoic acid, 2,6-difluorobenzoic acid, trans-3-(3-thienyl)acrylic acid, 6,13-bis(triisopropylsilylethynyl)-pentacene-2-carboxylic acid, 6,13-bis(triisopropylsilylethynyl)-pentacene-2-acrylic acid, 6,11-bis (triisopropylsilylethynyl)-tetracene-2-carboxylic acid, 6,11-bis(triisopropylsilylethynyl)-tetracene-2-acrylic acid, 5,10-bis(triisopropylsilylethynyl)-anthracene-2-carboxylic acid, 5,10-bis(triisopropylsilylethynyl)-anthracene-2-acrylic acid, naphthalene-2-carboxylic acid, and/or naphthalene-2-acrylic acid In some embodiments of the present disclosure, the nanocrystal core may have an average particle size between 1 nm and 100 nm. In some embodiments of the present disclosure, the nanocrystal core may include at least one of a Group II element, a Group III element, a Group IV element, a Group V element, Group VI element, and/or a noble metal. In some embodiments of the present disclosure, the nanocrystal core may include at least one of PbS, PbSe, PbTe, CdS, CdSe, CdTe, ZnS, ZnSe, ZnTe, HgS, HgSe, HgTe, GaN, GaP, GaAs, InP, InAs, Si, Ge, Au, Pt, Cu, Ni, $AgSbS_2$, $AgSbSe_2$, $CuInS_2$, $CuInSe_2$, CuInSSe, $Cu_2SnS_3$, $Cu_2SnSe_3$, CZTS (copper, zinc, tin, sulfide), CZTSe (copper, zinc, tin, selenium), and/or CZTSSe (copper, zinc, tin, sulfur, selenium). In some embodiments of the present disclosure, the nanocrystal core may include at least one of a uniformly mixed alloy type nanocrystal core, a core-shell type nanocrystal core, a dot-in-rod type nanocrystal core, a dot-on-rod type nanocrystal core, and/or a Janus particle type nanocrystal core.

In some embodiments of the present disclosure, the nanocrystal may further include an optical absorbance enhancement between 1.1 and 2.0. In some embodiments of the present disclosure, the nanocrystal may further include an ionization energy between 6.5 eV and 4.0 eV. In some embodiments of the present disclosure, the nanocrystal may further include a work function between 5.5 eV and 3.0 eV. In some embodiments of the present disclosure, the ligand may be coordinated to the surface by at least one of a covalent bond, an ionic bond, a van der Waals interaction, dipole-dipole interactions, and/or a hydrogen-bond. In some embodiments of the present disclosure, the ligand may be coordinated to the surface of the nanocrystal core by an ionic bond.

An aspect of the present disclosure is a mixture that includes a nanocrystal that includes a nanocrystal core and a ligand, and a solvent, where the ligand is coordinated to a surface of the nanocrystal core, and the solvent, the nanocrystal, and the ligand form at least one of a stable solution-phase colloid or a stable ink. In some embodiments of the present disclosure, the solvent may include at least one of a polar solvent and/or a non-polar solvent. In some embodiments of the present disclosure, the solvent may include at least one of toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, and/or water.

An aspect of the present disclosure is a method that includes adding an exchange ligand to a solution that includes a first solvent, a nanocrystal core, and a starting ligand, where the exchange ligand includes a functionalized aromatic molecule, the nanocrystal core includes at least one of a Group II element, a Group III element, a Group IV element, a Group V element, Group VI element, and/or a noble metal, the starting ligand is coordinated to a surface of the nanocrystal core to form a starting nanocrystal, the exchange ligand replaces at least a portion of the starting ligand coordinated to the surface, and the exchange ligand coordinates to the surface to produce a ligand-exchanged nanocrystal in the solution.

In some embodiments of the present disclosure, the solution may be maintained at a temperature between 20° C. and 30° C. In some embodiments of the present disclosure, the first solvent may include at least one of a polar solvent and/or a non-polar solvent. In some embodiments of the present disclosure, the first solvent may include at least one of dichloromethane, pentane, cyclohexane, hexane, heptane, octane, toluene, tetrachoroethylene, chloroform, and/or carbon tetrachloride.

BRIEF DESCRIPTION OF THE DRAWINGS

Some embodiments are illustrated in referenced figures of the drawings. It is intended that the embodiments and figures disclosed herein are to be considered illustrative rather than limiting.

REFERENCE NUMBERS

| 100 | starting nanocrystal |
|---|---|
| 110 | final nanocrystal |
| 120 | nanocrystal core |
| 122 | surface |
| 130 | starting ligand |
| 140 | exchange ligand |
| 200 | method |
| 210 | preparing |
| 212 | first solvent |
| 214 | first solution |
| 220 | adding exchange ligand |
| 222 | second solution |
| 230 | precipitating |
| 232 | precipitating agent |
| 234 | mixture |
| 240 | separating |
| 242 | liquid phase |
| 244 | solid phase |
| 250 | stabilizing |
| 252 | third solvent |
| 254 | ink |

DETAILED DESCRIPTION

The present disclosure may address one or more of the problems and deficiencies of the prior art. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

Figure 1:
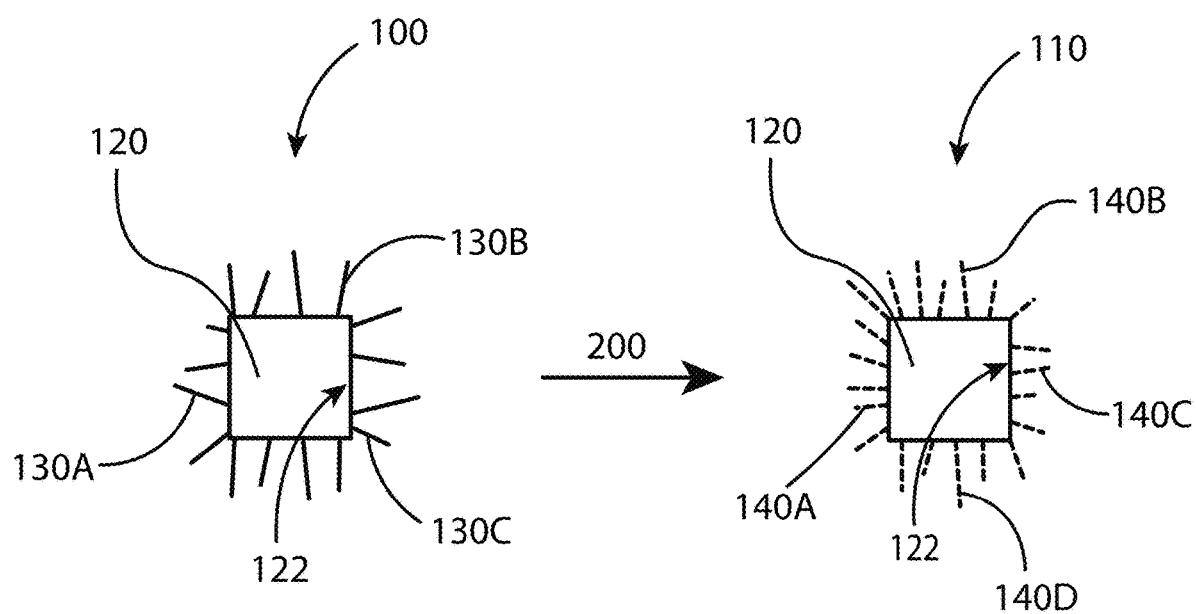
FIG. 1 illustrates a starting nanocrystal that includes a nanocrystal core and a starting ligand, and a final nanocrystal that includes the nanocrystal core and an exchange ligand, according to some embodiments of the present disclosure.

The present disclosure relates to ligand stabilized nanocrystal cores, in particular lead sulfide and/or lead selenide nanocrystal cores stabilized by functionalized aromatic molecules that are coordinated with one or more exposed surfaces of the nanocrystal cores. The present disclosure also relates to methods for producing ligand stabilized nanocrystal cores. FIG. 1 illustrates a starting nanocrystal 100 that includes a nanocrystal core 120 having at least one surface 122 such that a starting ligand 130 (e.g. 130A-C) can coordinate with the surface 122. As used herein, the term "coordinate" refers to a binding relationship between the nanocrystal core 120 and the ligand, in this case, the starting ligand 130. So, in general, a ligand coordinated with a surface of a nanocrystal core refers to at least one of a covalent bond, an ionic bond, a van der Waals interaction, dipole-dipole interactions, or a hydrogen-bond between the surface of the nanocrystal core and the binding group that attaches the ligand to the surface of the nanocrystal.

A nanocrystal core may be constructed of any suitable material with examples including Group II-VI elements, Group III-V elements, Group IV-VI elements, Group IV elements, a noble metal, a transition metal oxide, and/or a ternary, quaternary, or penternary compound, with examples including, but not limited to, PbS, PbSe, PbTe, CdS, CdSe, CdTe, ZnS, ZnSe, ZnTe, HgS, HgSe, HgTe, GaN, GaP, GaAs, InP, InAs, Si, Ge, Au, Ag, Pt, Cu, and Ni, AgSbS$_2$, AgSbSe$_2$, CuInS$_2$, CuInSe$_2$, CuInSSe, Cu$_2$SnS$_3$, Cu$_2$SnSe$_3$, CZTS, CZTSe, CZTSSe, or mixtures thereof. In some embodiments of the present disclosure, a nanocrystal core may be of substantially one material phase. In some embodiments of the present disclosure, a nanocrystal core may be of two or more material phases (e.g. a heterostructure nanocrystal core), such as at least one of a uniformly mixed alloy type nanocrystal core, a core-shell type nanocrystal core, dot-in-rod type nanocrystal core, dot-on-rod type nanocrystal core, and/or Janus particle type nanocrystal core. The nanocrystal core may have a characteristic length between 1 nm and 100 nm. The nanocrystal core may have a crystalline, semi-crystalline, or amorphous structure. The starting ligand may include at least one of alkyl carboxylate, alkyl amine, alkyl phosphine, alkyl phosphonate, or alkyl thiolate, or mixtures thereof.

Figure 3:
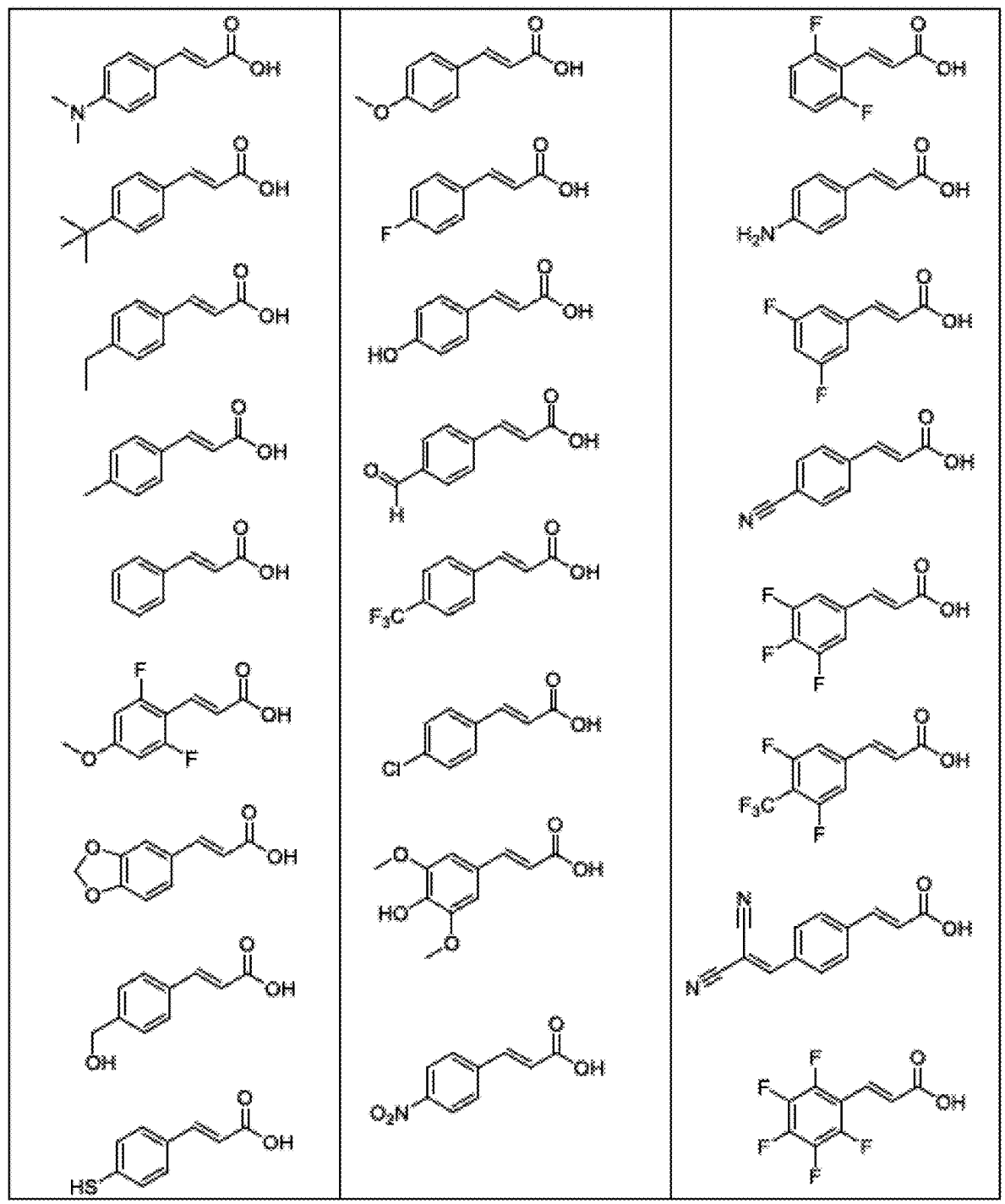
FIGS. 3-5 illustrate some examples of exchange ligands, according to some embodiments of the present disclosure.
Figure 4:
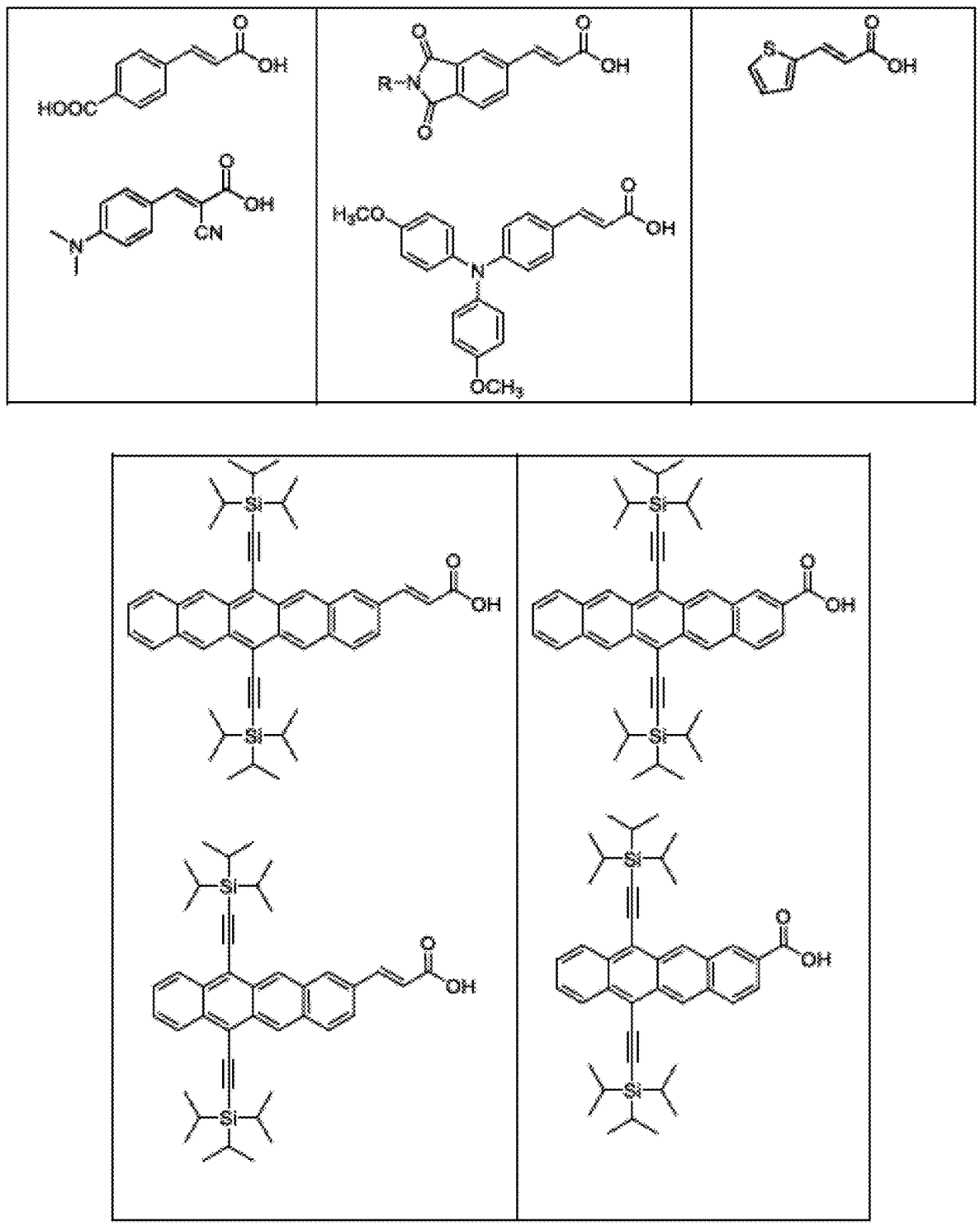
Figure 5:
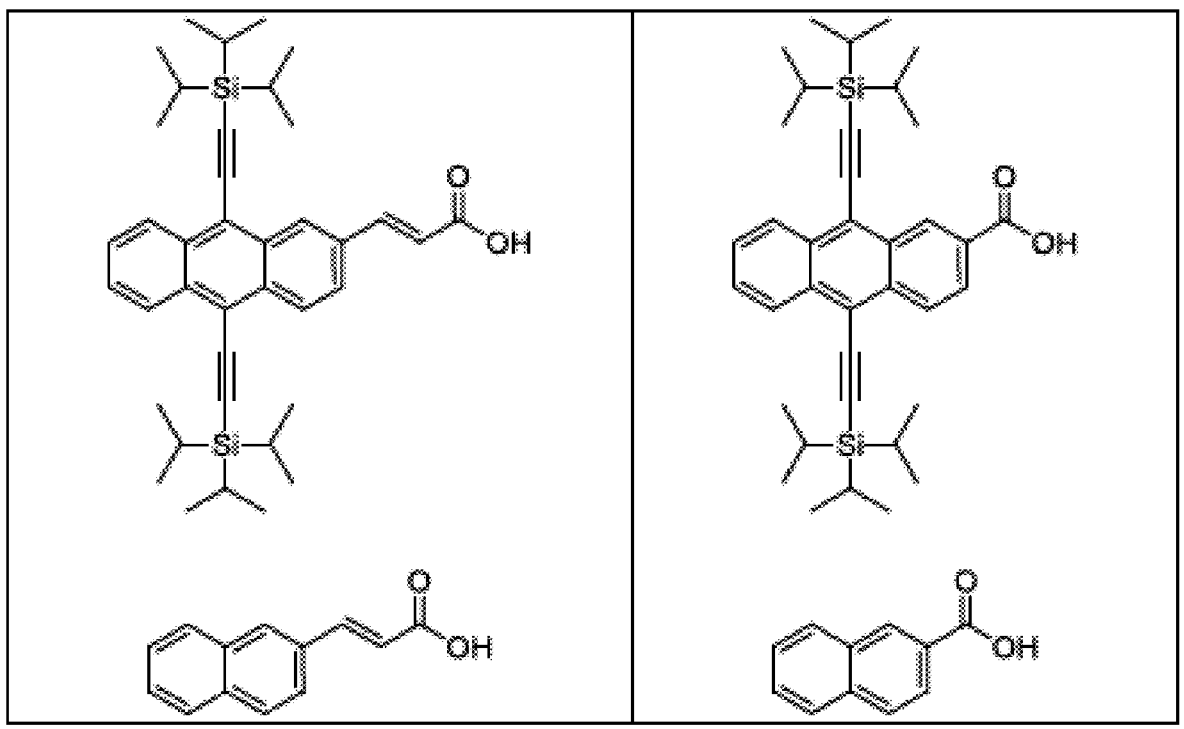

FIG. 1 illustrates that the starting nanocrystal 100 constructed of a nanocrystal core 120 coordinated with a starting ligand 130 may be transformed into a final nanocrystal 110 constructed of the nanocrystal core 120 coordinated with an exchange ligand 140 (e.g. 140A-140D) when treated according to an appropriate method 200, as described herein. The method 200 results in an exchange of at least a portion of the starting ligand 130 coordinated with a surface 122 of the nanocrystal core 120 by the exchange ligand 140. As a result, the final nanocrystal 110 includes at least some exchange ligand 140 coordinated to the surface 122 of the nanocrystal core 120. In some embodiments of the present disclosure, substantially all of the starting ligand 130 may be removed from the surface 122 of the nanocrystal core 120, such that substantially all of the available surface 122 may coordinate with the exchange ligand 140. In some embodiments of the present disclosure, a fraction of the starting ligand 130 may be removed from the surface 122 of the nanocrystal core 120, such that only a portion of the surface 122 may coordinate with the exchange ligand 140. Suitable exchange ligands 140 include at least one ligand represented by,

B-L-A-R$_4$ where B is a binding group that coordinates the ligand to the surface of the nanocrystal core, where B includes, for example, —CN, —COOH, —CSSH, —SH, —NR$_2$, —POOOH (where R is a hydrogen atom or a saturated and/or unsaturated aliphatic hydrocarbon group), and/or any other suitable functional group. L is a linking group between the binding group (B) and backbone (A), where the linking group may be linked to B and A by direct bond and may be for example, an aliphatic organic group and/or an aromatic organic group. The backbone group (A) may include, for example, a single carbon atom, a benzene ring, a polyacene, and/or any other suitable aromatic molecule. R$_4$ is a functional group, and may include for example any combination of substitutional groups described by Hansch (Chem. Rev. 91, 165, (1991)), which is incorporated by reference herein in its entirety, and placed at any position(s) on the ligand aromatic backbone or linking group. Examples of some suitable exchange ligands are illustrated in FIGS. 3-5.

Thus, in some embodiments of the present disclosure, an exchange ligand may be a functionalized aromatic molecule, for example cinnamic acid (CAH) or a functionalized CAH. Other examples of functionalized aromatic molecules include at least one of 2,3,4,5,6-pentafluorocinnamic acid, 3,5-bis(trifluoromethyl)cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tert-butylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino)cinnamic acid, 3,4-(2,5-pyrrolidinedione) cinnamic acid, styrylphosphonic acid, 4-formyl styrylphosphonic acid, (4-(2,2-dicyanovinyl)styryl)phosphonic acid, 2,6-difluorostyrylphosphonic acid, 4-trifluoromethylstyrylphosphonic acid, 4-methoxystyrylphosphonic acid, 3-methylstyrylphosphonic acid, benzoic acid, 4-methylbenzoic acid, 4-mercaptobenzoic acid, 4-methoxybenzoic acid, 4-fluorobenzoic acid, 4-hydroxybenzoic acid, 4-nitrobenzoic acid, 4-cyanobenzoic acid, 4-formylbenzoic acid, 4-trifluoromethylbenzoic acid, 4-chlorobenzoic acid, 4-bromobenzoic acid, 4-iodobenzoic acid, 4-fluorobenzoic acid, 2,6-difluorobenzoic acid, trans-3-(3-thienyl)acrylic acid, 6,13-bis(triisopropylsilylethynyl)-pentacene-2-carboxylic acid, 6,13-bis(triisopropylsilylethynyl)-pentacene-2-acrylic acid, 6,11-bis(triisopropylsilylethynyl)-tetracene-2-carboxylic acid, 6,11-bis(triisopropylsilylethynyl)-tetracene-2-acrylic acid, 5,10-bis(triisopropylsilylethynyl)-anthracene-2-carboxylic acid, 5,10-bis(triisopropylsilylethynyl)-anthracene-2-acrylic acid, naphthalene-2-carboxylic acid, and/or naphthalene-2-acrylic acid.

Figure 2:
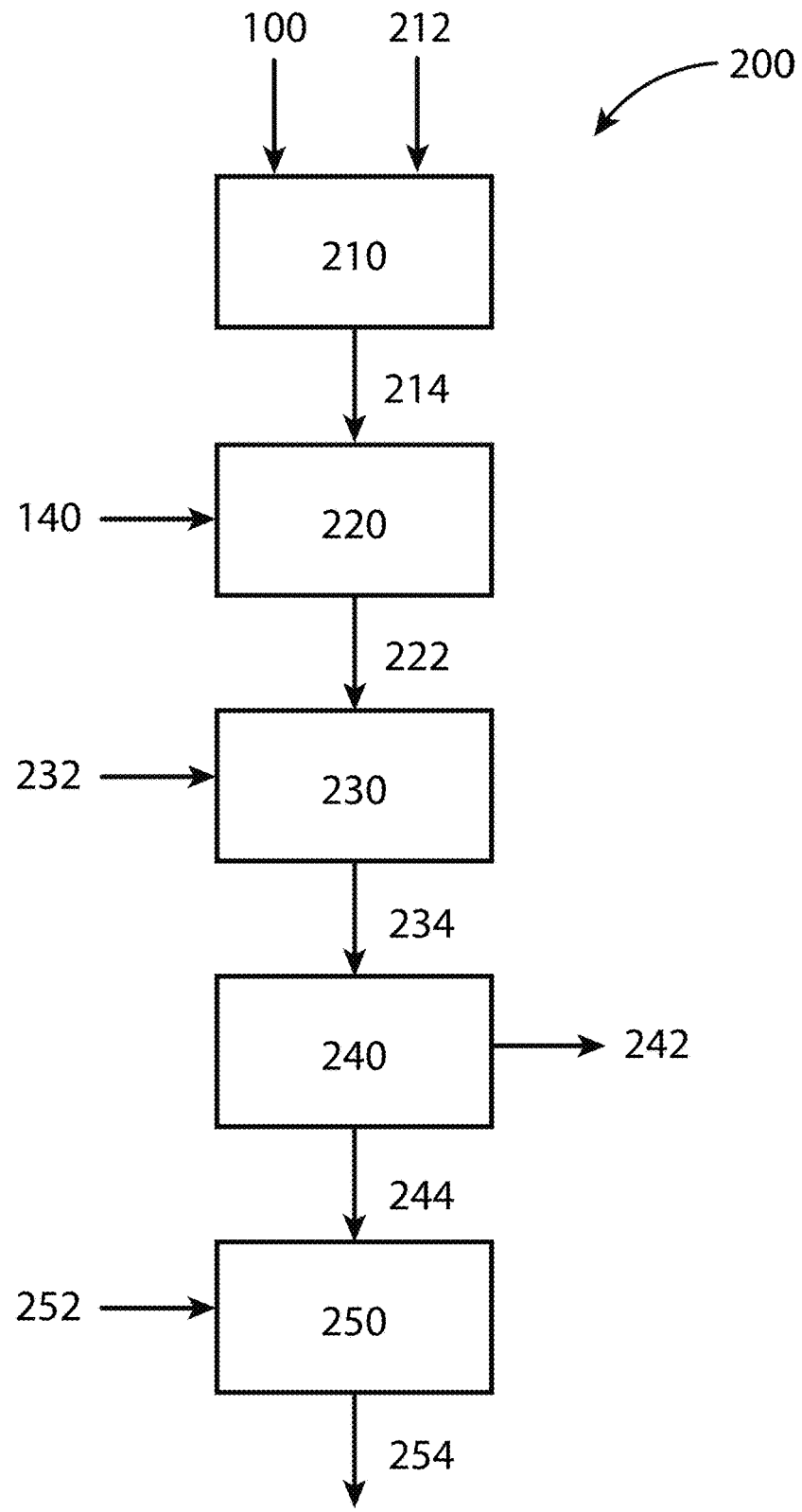
FIG. 2 illustrates a method for converting a starting nanocrystal that includes a nanocrystal core and a starting ligand to a final nanocrystal that includes the nanocrystal core and an exchange ligand, according to some embodiments of the present disclosure.

FIG. 2 illustrates a method 200 for producing a stable colloid and/or ink 254 that includes stabilized nanocrystals as described above and shown in FIG. 1. In the example of FIG. 2, the method 200 begins with the preparing 210 of a first solution 214 by combining a starting nanocrystal 100 (as described above that includes the nanocrystal core 120 coordinated with the starting ligand 130) with a first solvent 212. The first solvent 212 may be any suitable solvent having a suitably high solubility for the starting nanocrystal 100. So, the choice of the first solvent 212 may depend on at least one of the starting nanocrystal 100 and/or the final nanocrystal 110 chosen for a specific recipe for the ink 254. Thus, the first solvent 212 may be a polar solvent and/or a non-polar solvent with examples including toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, and/or water. The first solution 214 may be prepared in any suitable vessel and/or equipment (e.g. a stirred tank, static mixer, chromatography column) in either a continuous mode, semi-continuous mode, and/or batch mode.

Once the first solution 214 containing the starting nanocrystal 100 of the starting ligand 130 coordinated to a surface 122 of the nanocrystal core 120 is complete, the method 200 may proceed with the adding 220 of the exchange ligand 140 to the first solution 214, resulting in the formation of a second solution 222. In some embodiments of the present disclosure, the adding 220 of the exchange ligand 140 may occur in the same unit operation (e.g. stirred tank) that was used to make the first solution 214. In some embodiments of the present disclosure, the adding 220 of the exchange ligand 140 may occur in a separate piece of equipment. The adding 220 may be completed in any suitable vessel and/or equipment (e.g. a stirred tank, static mixer, chromatography column) in either a continuous mode, semi-continuous mode, and or batch mode. The exchange ligand 140 may be added to the first solution 214 such that the ratio of the exchange ligand 140 to the nanocrystal core 120 in the second solution 222 is between 1:1 and 1000:1. In some embodiments of the present disclosure, the exchange ligand 130 may be mixed with a second solvent 232 to form a solution (not shown) containing the exchange ligand 130, such that this solution is added to the first solution 214 shown in FIG. 2. The second solvent 232 may be any suitable solvent having a suitably high solubility for the exchange ligand 140. Thus, the second solvent 232 may be a polar solvent and/or a non-polar solvent with examples including toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, and/or water. In some embodiments of the present disclosure, the solution containing the exchange ligand 130 may be added to the first solution 214 utilizing a static mixer and/or a stirred tank reactor and/or a size-exclusion chromatography column.

The adding 220 of the exchange ligand 140 to the first solution 214 results in the partial or complete exchange of the starting ligand 140 coordinated to a surface 122 of the nanocrystal core 120 with the exchange ligand 140, such that at least some of the surface 122 of the nanocrystal core 120 is coordinated with the exchange ligand 140.

In some embodiments of the present disclosure, the final nanocrystal 110 of the exchange ligand 140 coordinated to the nanocrystal core 120 may be substantially soluble in the second solution 222, although depending on the process conditions and components chosen for a specific application, the final nanocrystal 110 may be only partially soluble. Thus, in some embodiments of the present disclosure, the final nanocrystal 110 may have a first soluble component and a second, insoluble, solid-phase component. However, for the example shown in FIG. 2, the final nanocrystal 110, contained in the second solution 222, is substantially dissolved (e.g. where substantially is greater than 80%, or >90%, or >99%) in the second solution 222. As a result, the method 200 may proceed with precipitating 230 of the final nanocrystal 110 from the second solution 222, where the precipitating 230 is induced by the addition of a precipitating agent 232 to the second solution 222, resulting in the formation of a mixture 234 containing both a liquid phase and a precipitate of the final nanocrystal 110. As used herein, a precipitating agent 232 is any compound capable of reducing the solubility of the final nanocrystal 110 in the second solution 222 to the point where a significant fraction of the final nanocrystal 110 comes out of solution in the solid form. Thus, in some embodiments of the present disclosure, the precipitating agent 232 may include a third solvent (not shown). This third solvent may be any suitable polar and/or non-polar solvent with examples including at least one of pentane, cyclohexane, hexane, heptane, octane, toluene, acetone, acetonitrile, methanol, and/or ethanol. Alternatively, the temperature of the second solution 222 can be lowered such that the solubility of the final nanocrystal 110 in the second solution 222 is reduced to the point where a significant fraction of the final nanocrystal 110 comes out of solution in the solid form. The precipitating 230 may be achieved in the same unit operation used to perform the preparing 210 and the adding 220. Such a scenario may be desirable for batch operations. However, in some embodiments of the present disclosure, the precipitating 230 may be achieved in a separate unit operating; e.g. in a continuous stirred tank for larger-scale continuous operations.

Referring again to FIG. 2, a method 200 may proceed by treating the mixture 234 by separating 240 the final nanocrystal 110 from the mixture 234, resulting in the formation of a solid phase 244 containing the final nanocrystal 110 and a liquid phase 242 that is substantially free of the final nanocrystal 110. In some embodiments of the present disclosure, the separating 240 may be achieved by any suitable solid-liquid separation unit operation with examples including filtration, centrifugation, and/or electrostatic separation methods.

In the example method 200 shown in FIG. 2, the method 200 may conclude by stabilizing 250 the solid phase 244 containing the final nanocrystal 110 to form the final targeted ink 254. In some embodiments of the present disclosure, the ink 254 may be formed by the addition of a third solvent 252 to the solid phase 244. In this case, it is desirable to choose a third solvent 252 for which the final nanocrystal 110 has a high colloidal stability so as to maintain a large percentage of the final nanocrystal 110 in the solution phase when mixed with the third solvent. Thus, depending on the other process conditions and the physical properties of the final nanocrystal 110, any suitable third solvent mixture 252 may be used with example components including toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, and/or water.

It should be noted that although the example method 200 described above and illustrated in FIG. 2 describe the use of three solvents, three solvent are not necessarily required, either to produce the final nanocrystal 110 and/or the ink 254. In most situations at least one solvent will be needed, e.g. for the adding 220 of the exchange ligand 140 to the starting nanocrystal 100 to achieve the exchange of at least a portion of the starting ligand 130 with the exchange ligand 140, as described above. So, it is conceivable that alternative methods may involve a single solvent containing the starting nanocrystal 100 to which the exchange ligand 140 is added or a single solvent containing the exchange ligand 140 to which the starting nanocrystal 100 is added. Subsequent method steps, e.g. precipitating 230 and/or stabilizing 250, may be accomplished by other means; e.g. by changing the concentration of the same solvent used in the adding 220 and/or by changing the temperature of at least one of the first solution 212, the second solution 222, and/or the mixture 234. These and other variations of the method 200 shown in FIG. 2 are considered to be within the scope of the present disclosure.

The present disclosure relates to solution phase ligand exchange methods for modifying nanocrystals (also referred to herein as quantum dots), including nanocrystals having PbS nanocrystal cores, where the exchange ligands include functionalized aromatic organic molecules. The present disclosure describes large-scale solution-phase ligand exchanges that completely replaced starting ligands such as oleate ligands with functionalized aromatic organic acid molecule exchange ligands. The present disclosure relates to methods that enable the design of nanocrystals, nanocrystal-containing materials, and/or nanocrystal-containing systems having specific enhanced performance metrics, for example, broadband optical absorbance and absolute band edge energy level shifts. For the specific case of cinnamic acid exchange ligands, eight different functionalized cinnamic acid ligands (molecules) were extensively characterized and tested. For these eight exchange ligands, HOMO/LUMO energy gaps between about 3 eV and about 5 eV and dipole moments between about −6 Debye to 8 Debye were measured, while the ligand/nanocrystal core surface coordination (carboxylate moiety) remained the same. Thus, the present disclosure describes specific nanocrystal-containing materials and/or system design methods that enable enhancement of the nanocrystals', nanocrystal-containing materials', and/or nanocrystal-containing systems' broadband optical absorbances (up to a factor of two) and shift the absolute nanocrystal systems' band edge energy levels (over 2.0 eV). The work function of the PbS-(cinnamic acid molecule ligand) systems was shown to be tunable between about 3.0 eV and about 5.4 eV, while maintaining the Fermi-level position within the nanocrystal bandgap, and was shown to correlate to the dipole moment of the ligand, as well as the amount of ligand bound to the surface of the nanocrystal core. These nanocrystal design methods are supported by theoretical calculations, which provide guidance for designed material applications for use in next generation photovoltaic devices, light-emitting diodes (LEDs), and/or photodetectors.

Examples

Model Nanocrystal System: In this example, starting nanocrystals (constructed of starting nanocrystal cores coordinated with starting ligands) consisted of 3.2 nm diameter PbS nanocrystal cores coordinated with oleate starting ligands, which yielded a first exciton transition energy centered around 1.3 eV. A synthetic protocol was employed that ensures a well-defined, hydroxide free nanocrystal core surface. First, Pb(oleate)$_2$ was synthesized directly from PbO and oleic acid (OAH), which was then reacted with diphenylthiourea to produce oleate (OA$^-$) coordinated to PbS nanocrystal cores with a narrow size distribution on a multi-gram scale. A large starting nanocrystal yield allowed for all the experiments reported herein to be performed using the same batch of starting nanocrystals, thereby limiting the variability in starting nanocrystals used between individual experiments.

The following description includes eight functionalized cinnamic acid exchange ligands (R-CAHs) (see FIG. 6) that preserve the OA$^-$ surface coordinating environment and Pb:S nanocrystal core stoichiometric ratio upon ligand exchange. The dipole moment and HOMO-LUMO gap of the ligands are widely tunable through functionalization of the aromatic ring, and the vinyl linkage allows for electronic coupling to the nanocrystal core while ensuring good colloidal stability. Each functionalized cinnamic acid ligand is denoted by its functional group and whether it is protonated, free in solution or deprotonated and bound to the surface of the nanocrystal core. Thus, 4-H-CAH denotes a trans-cinnamic acid ligand and 4-H-CA$^-$ denotes a trans-cinnamate$^-$ ligand bound to the nanocrystal core. The HOMO/LUMO levels for each functionalized cinnamic acid ligand were calculated and compared to measured values (see Panel A of FIG. 6) determined using a combination of optical absorbance and cyclic voltammetry. The dashed lines represent a k·p calculation of 3.2 nm PbS nanocrystal core $1S_e$ and $1S_h$ energy levels. Ligand properties were calculated using the plane wave basis set code Quantum-ESPRESSO using the PBE parametrization of the generalized gradient approximation exchange-correlation functional. It was determined that the calculated ligand dipoles are proportional to their corresponding Hammett constants, which denotes the electron withdrawing character of the aromatic functional group.

Figure 6:
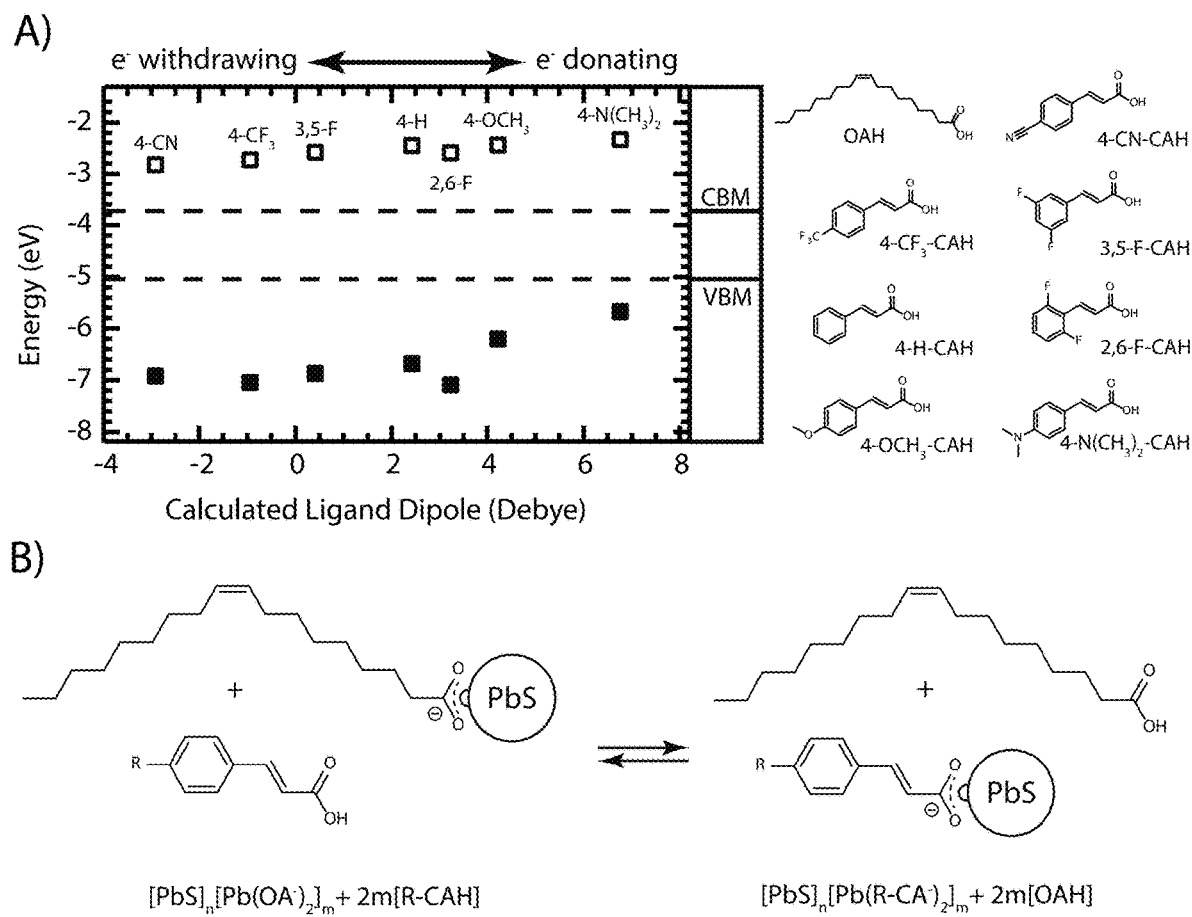
FIG. 6 illustrates a model nanocrystal system, according to some embodiments of the present disclosure; (Panel A, left) Calculated (diamonds) and experimentally determined (squares) HOMO (closed points) and LUMO (open points) energy levels versus the calculated ligand dipole. The HOMO/LUMO levels trend toward vacuum with more electron donating character (positive dipole). Dashed gray lines represent calculated PbS nanocrystal energy levels. Labels correspond to the aromatic functionalization group(s) of the ligand structures displayed in (Panel A, right) and are used throughout this work. $4(CN)_2$-CAH=4-(2,2-Dicyanovinyl)cinnamic Acid; 4CN-CAH=4-Cyanocinnamic Acid; $4CF_3$-CAH=4-Trifluoromethylcinnamic Acid; 35F-CAH=3, 5-Difluorocinnamic Acid; 4H-CAH=Cinnamic Acid; 26F-CAH=2,6-Difluorocinnamic Acid; $40CH_3$-CAH=4-Methoxycinnamic Acid; $4N(CH_3)_2$-CAH=4-Dimethylaminocinnamic Acid (Panel B) X-type ligand exchange in which surface bound oleate$^-$ is displaced by functionalized cinnamic acid molecules.

In some embodiments of the present disclosure, a solution-phase ligand exchange procedure resulted in the efficient replacement of initial OA$^-$ by R-CAHs to form R-CA$^-$ passivated PbS nanocrystal cores through an X-type ligand exchange (see Panel B of FIG. 6). Without wishing to be bound by theory, incoming free R-CAHs may transfer a proton to a surface bound OA$^-$ to form free OAH and surface bound R-CA$^-$. Since there is no other source of protons in the system, the exchange may be 1:1 and adding excess of R-CAH may drive the exchange towards completion.

Figure 7:
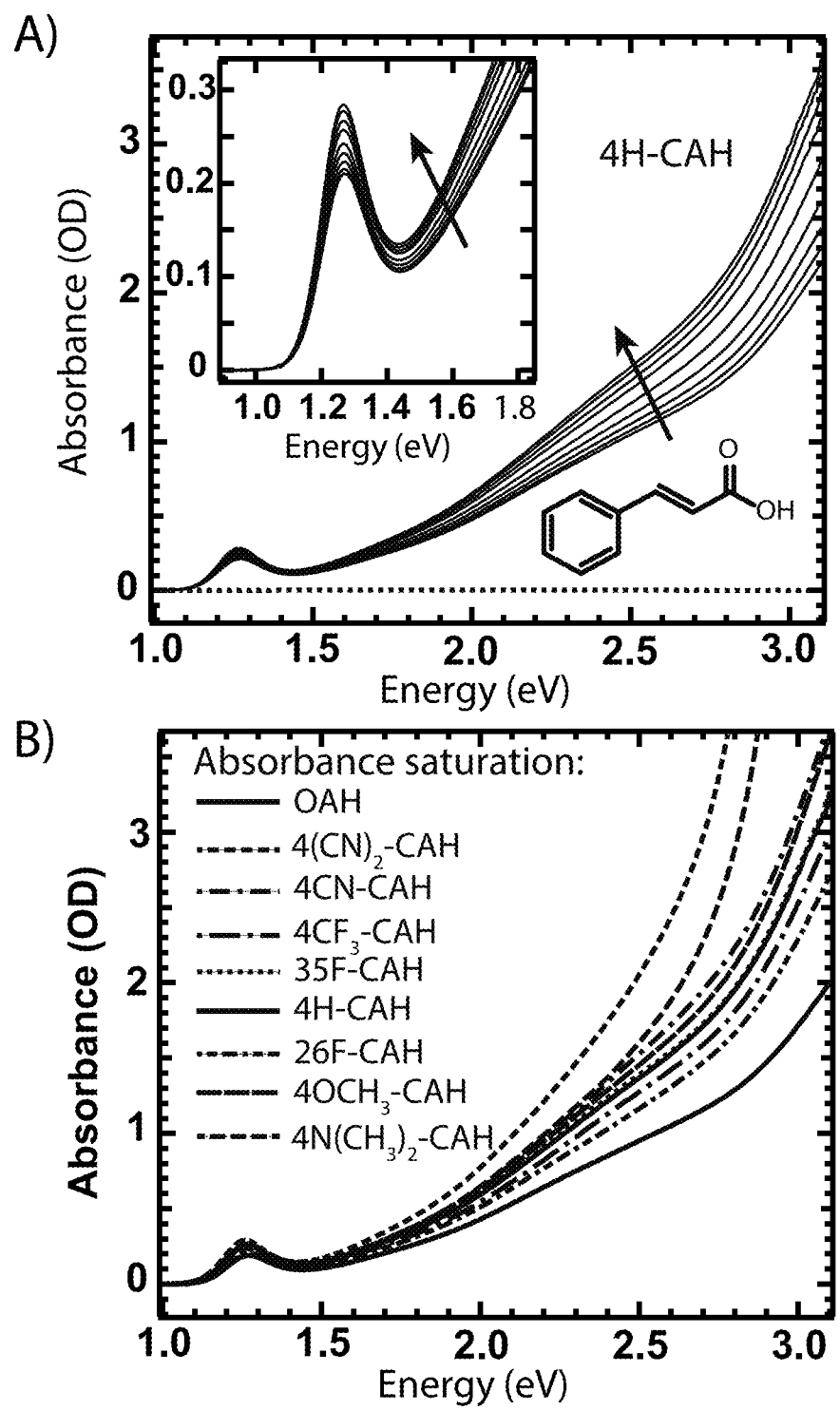
FIG. 7 illustrates quantitative solution-phase ligand exchange absorbance experiments, according to some embodiments of the present disclosure; Panel A Absorbance spectra of $OA^-$ passivated (bold dashed), fully 4H-CA$^-$ exchanged (bold solid) PbS nanocrystals, and neat 4H-CAH (light gray at 0). The dark gray spectra are those of partially exchanged R-CA$^-$/nanocrystals. The inset shows the first exciton absorbance feature. Panel B absorbance spectra of the fully exchanged R-CA$^-$/nanocrystals compared to the stock $OA^-$/nanocrystals.
Figure 17:
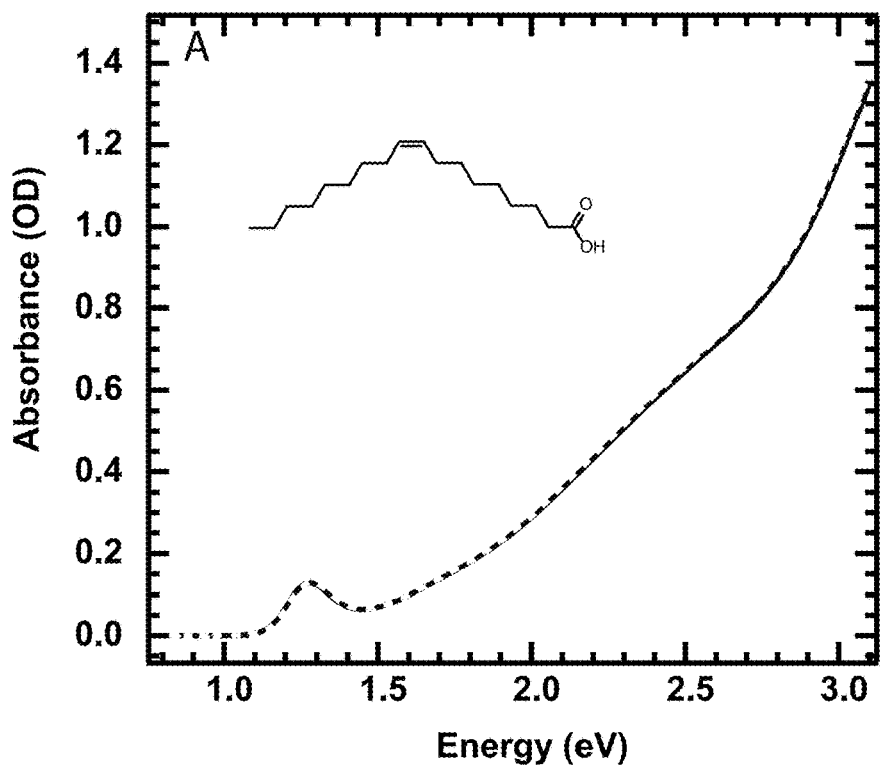
FIG. 17 illustrates (Panel A) spectrophotometric titration of PbS $OA^-$/nanocrystals with OAH, according to some embodiments of the present disclosure. The solid line is the absorbance spectrum of the stock $OA^-$/nanocrystal solution and the dashed line is that after 1000 equivalents of OAH. Absorbance spectra taken at lower equivalents of added OAH are similar. (Panel B) First exciton absorbance feature for as synthesized (dashed) and R-CA$^-$ passivated (solid) PbS nanocrystal cores. The peak energies change as a function of ligand identity. The ligands with electron donating (withdrawing) character cause the peak energy to blue (red) shift, and the degree of the induced shift is proportional to the observed film work function shift. Such shifts suggest the surface dipole applied by a ligand shell influences electron and hole wave function delocalization within and outside of the nanocrystal core, thus affecting quantum confinement.
Figure 17:
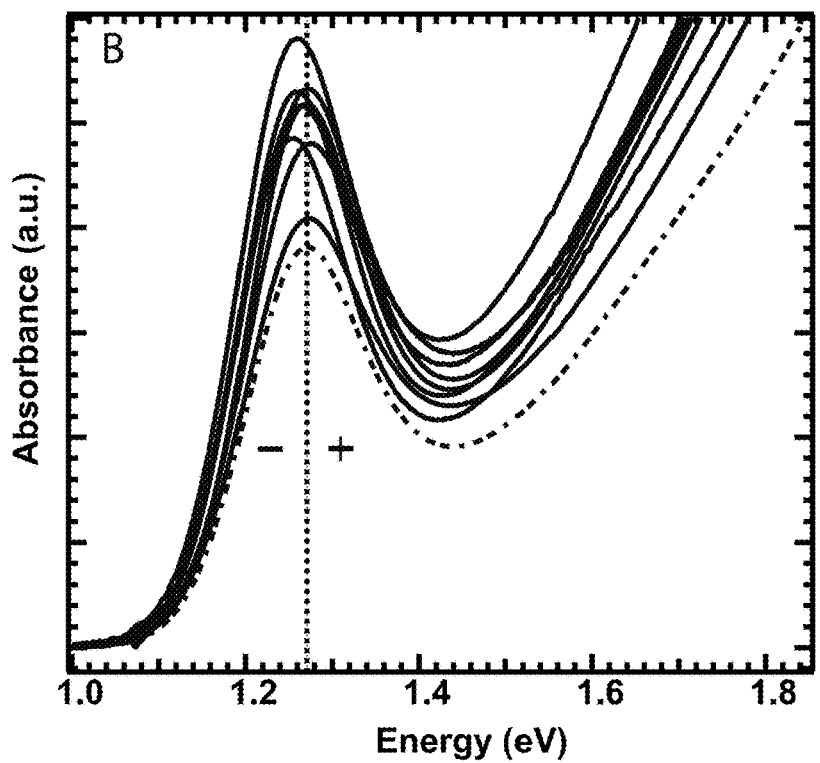

Design Parameter—Enhanced Optical Absorption: As shown herein, it was determined that the addition of a solution containing R-CAH exchange ligand to a solution of OA$^-$ coordinated with nanocrystal cores results in; (1) a sharpening of the first exciton absorbance feature (see the inset to Panel A of FIG. 7 and FIGS. 13-16) and; (2) an increase in the broadband absorbance (Panel A of FIG. 7 for 4-H-CAH). Increasing the amount of ligand resulted in further absorbance enhancement (Panel A of FIG. 7) until it saturated, at which point the nanocrystals were fully exchanged (top trace, Panel A of FIG. 7). It was verified that upon addition of OAH to OA$^-$/nanocrystal cores that the absorption did not change (see Panel A of FIG. 17). FIGS. 13-16 show the raw absorbance data for the other seven functionalized cinnamic acid exchange ligands. Compiled optical absorbance for the fully R-CA$^-$ exchanged nanocrystals is shown in Panel B of FIG. 7, where each spectra is normalized to the absorbance of the OA$^-$/nanocrystal cores. In each case the optical absorption was enhanced over the OA$^-$/nanocrystal cores. Thus, it can be concluded that the optical properties of colloidal nanocrystals are not simply determined by the nanocrystal core size and composition.

Figure 8:
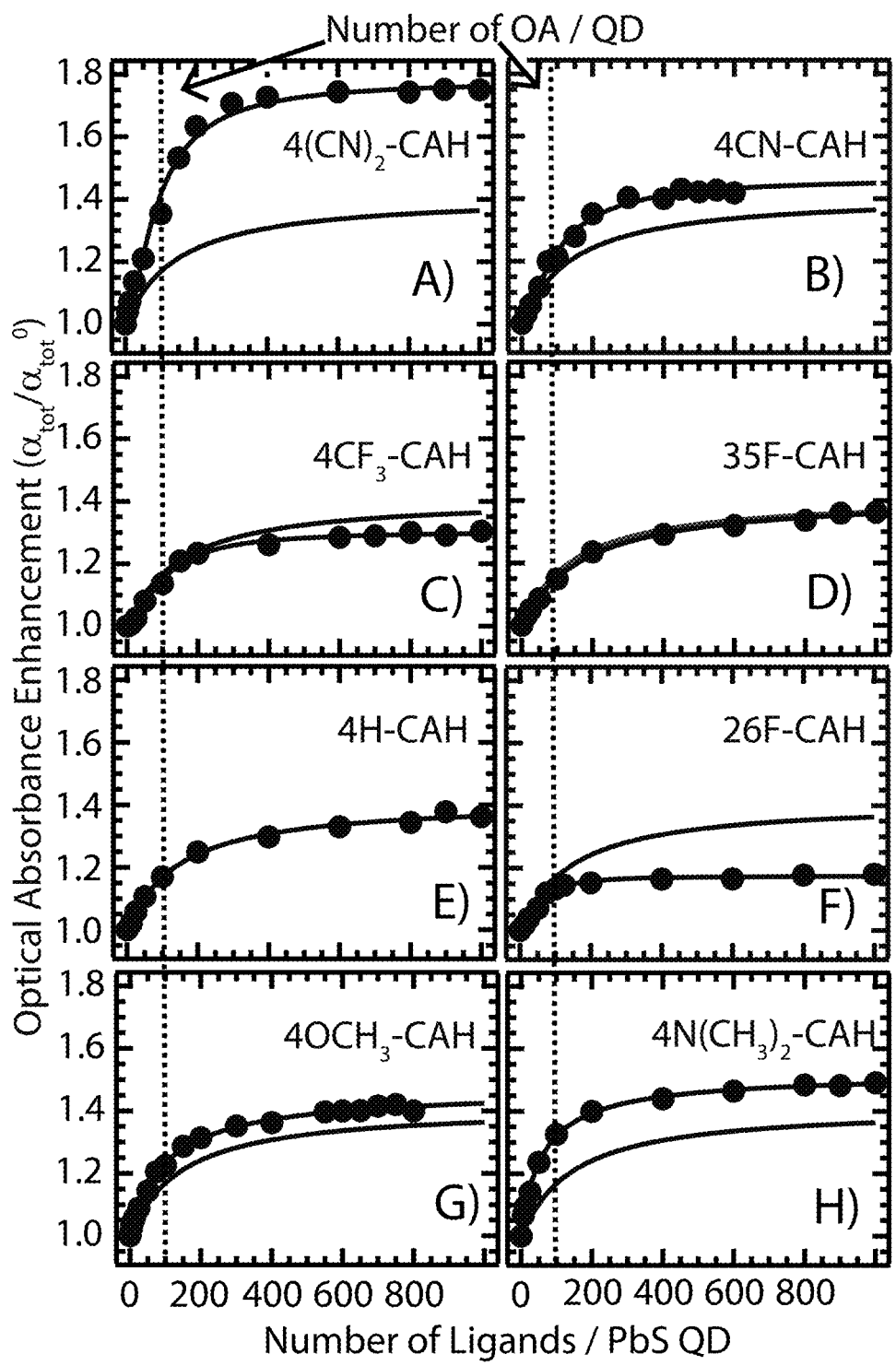
FIG. 8 Panels A-H illustrate $\alpha_{tot}/\alpha_{tot}^0$ as a function of ligand equivalents added per PbS nanocrystal. The dashed vertical line indicates 100 $OA^-$ ligands per nanocrystal. The solid lines are the best fits from a Hill Isotherm model (see Table 1). The solid lines without symbols on each panel is the best fit from the 4H-CAH as a comparison.
Figure 18:
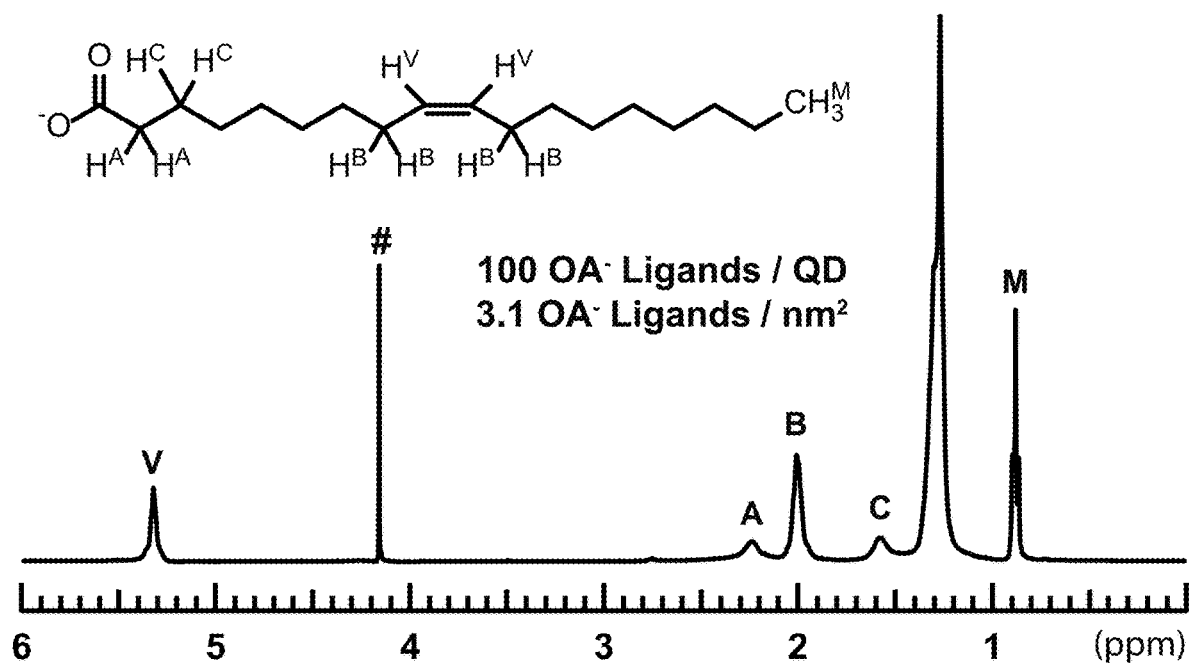
FIG. 18 illustrates quantitative $^1$H NMR of as-synthesized, OA$^-$ capped PbS nanocrystal cores in CDCl$_3$, according to some embodiments of the present disclosure. Surface bound oleate ligand density was estimated using a combination of UV-Vis-NIR and $^1$H NMR spectra. First, the concentration of a TCE solution of nanocrystals was standardized using UV-Vis-NIR absorbance at 400 nm. The addition of a known amount of ferrocene (10 H's) as an internal standard to the nanocrystal NMR sample allowed us to estimate the total number of surface bound oleate ligands using the well-resolved vinyl proton peak (H$^V$). We find that there are approximately 100 ligands per PbS nanocrystal core, giving an estimated OA$^-$ surface grafting density of 3.1 ligands/nm$^2$.

Quantitative spectrophotometric titrations were performed to learn more about the ligand exchange and determine the necessary ratio of R-CAH to add per PbS nanocrystal core to drive a complete exchange for a single, large-scale exchange procedure. To quantify the absorbance enhancement using a single number, $\alpha_{tot}/\alpha_{tot}^0$, was used, where $\alpha_{tot}$ is the integration of the fully R-CA$^-$ exchanged nanocrystal absorbance spectrum and $\alpha_{tot}^0$ is that of the OA$^-$/nanocrystal core spectrum in a similar solvent system. The integration started below the 1S exciton and ended prior to any ligand absorbance feature, 1.0-2.5 eV here. For all of the R-CAH ligands disclosed herein, there is a sharp increase in $\alpha_{tot}/\alpha_{tot}^0$ at low ligand addition equivalents with a subsequent plateau and saturation at larger equivalents, see Panels A-H of FIG. 8, which indicate fully ligand exchanged nanocrystals. In Panels A-H of FIG. 8, the dashed vertical black line indicates the number of OA$^-$ ligands per nanocrystal core determined by quantitative $^1$H NMR (See FIG. 18), which is approximately 100 ligands/nanocrystal core corresponding to 3.1 ligands/nm$^2$. It was determined that $\alpha_{tot}/\alpha_{tot}^0$ for the R-CA$^-$/nanocrystal core systems always plateaus at larger ligand equivalents than the number of native OA$^-$ originally coordinating with the nanocrystal core, which suggests that the ligand exchanges are governed by an equilibrium between surface bound ligands and free ligands that is driven towards surface bound R-CA$^-$ by the addition of excess R-CAH. The solid lines in Panels A-H of FIG. 8 are the best-fit lines of a Hill isotherm model to the data (see below) and the best-fit parameters are tabulated in Table 1 below.

Figure 9:
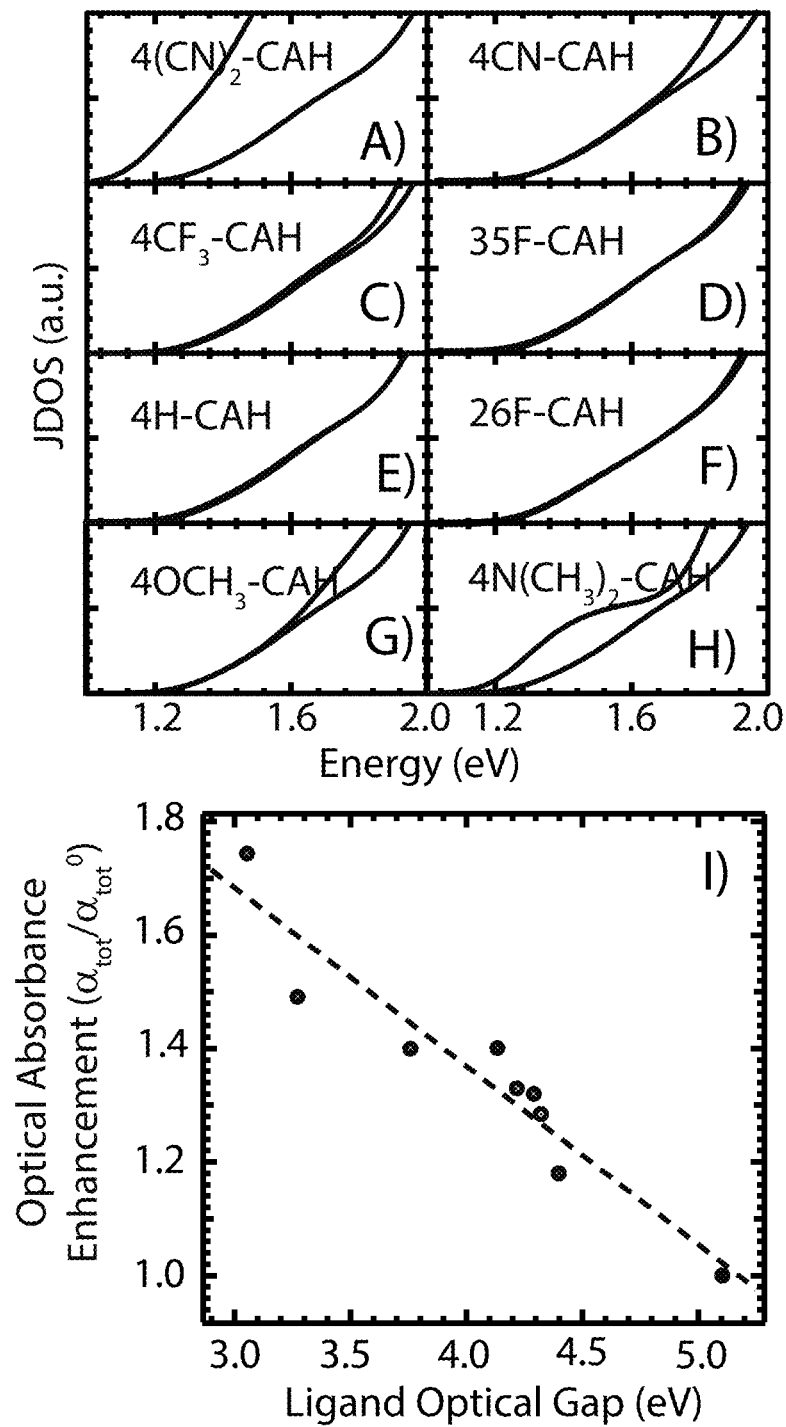
FIG. 9 Panels A-H illustrate joint density of states (DOS) computed for R-CA$^-$/nanocrystal models. The Joint DOS is resolved for transitions with mainly nanocrystal→nanocrystal (below second curve to the right) and either nanocrystal→ligand or ligand→nanocrystal character (above first curve). Panel I illustrates the relationship between $\alpha_{tot}/\alpha_{tot}^0$ and ligand optical gap.

To investigate the underlying cause of the enhanced absorption, density functional theory (DFT) calculations were performed on small PbS R-CA$^-$/nanocrystal core models (See below), which resulted in similar qualitative trends for the enhanced absorption as in the experiments. The calculated absorption was then decomposed into contributions of optical transitions that have mostly QD→QD (e.g. nanocrystal core→nanocrystal core) character and those with substantial ligand character (nanocrystal core→ligand, ligand→nanocrystal core). The decomposition was performed at the joint density of states (DOS) level (constant dipole matrix element approximation) and displayed in Panels A-H of FIG. 9. The nanocrystal core→nanocrystal core transitions remained constant for each ligand, while the transitions with ligand/nanocrystal core state mixing (nanocrystal core→ligand or ligand→nanocrystal core) were substantially increased for ligands with the lowest energy HOMO-LUMO transition. Since the number of ligand related transitions can only increase if their occupied (unoccupied) states are sufficiently aligned/mixed with nanocrystal core states, the ligands with the lowest energy HOMO-LUMO transition may give rise to the largest state mixing. Indeed, Panel I of FIG. 9 shows that the experimental enhanced absorbance of the ligand/nanocrystal core complex is greatest when the absorbance onset/optical gap of the ligands is the lowest.

TABLE 1

| | Langmuir Isotherm | | Hill Isotherm | | |
|---|---|---|---|---|---|
| | $(\alpha_{tot}/\alpha_{tot}^0)_{max}$ | $K_L$ | $(\alpha_{tot}/\alpha_{tot}^0)_{max}$ | $K_H$ | n |
| 4(CN)$_2$—CAH | 1.88 | 0.0089 | 1.79 | 91.7 | 1.55 |
| 4CN—CAH | 1.55 | 0.0069 | 1.47 | 102.1 | 1.44 |
| 4CF$_3$—CAH | 1.35 | 0.0073 | 1.30 | 101.6 | 1.61 |
| 35F—CAH | 1.42 | 0.0056 | 1.41 | 168.0 | 1.05 |
| 4H—CAH | 1.42 | 0.0066 | 1.41 | 141.9 | 1.05 |
| 26F—CAH | 1.19 | 0.0162 | 1.17 | 53.5 | 1.72 |
| 4OCH$_3$—CAH | 1.47 | 0.0099 | 1.47 | 102.5 | 0.98 |
| 4N(CH$_3$)$_2$—CAH | 1.51 | 0.0170 | 1.52 | 61.7 | 0.95 |

Figure 10:
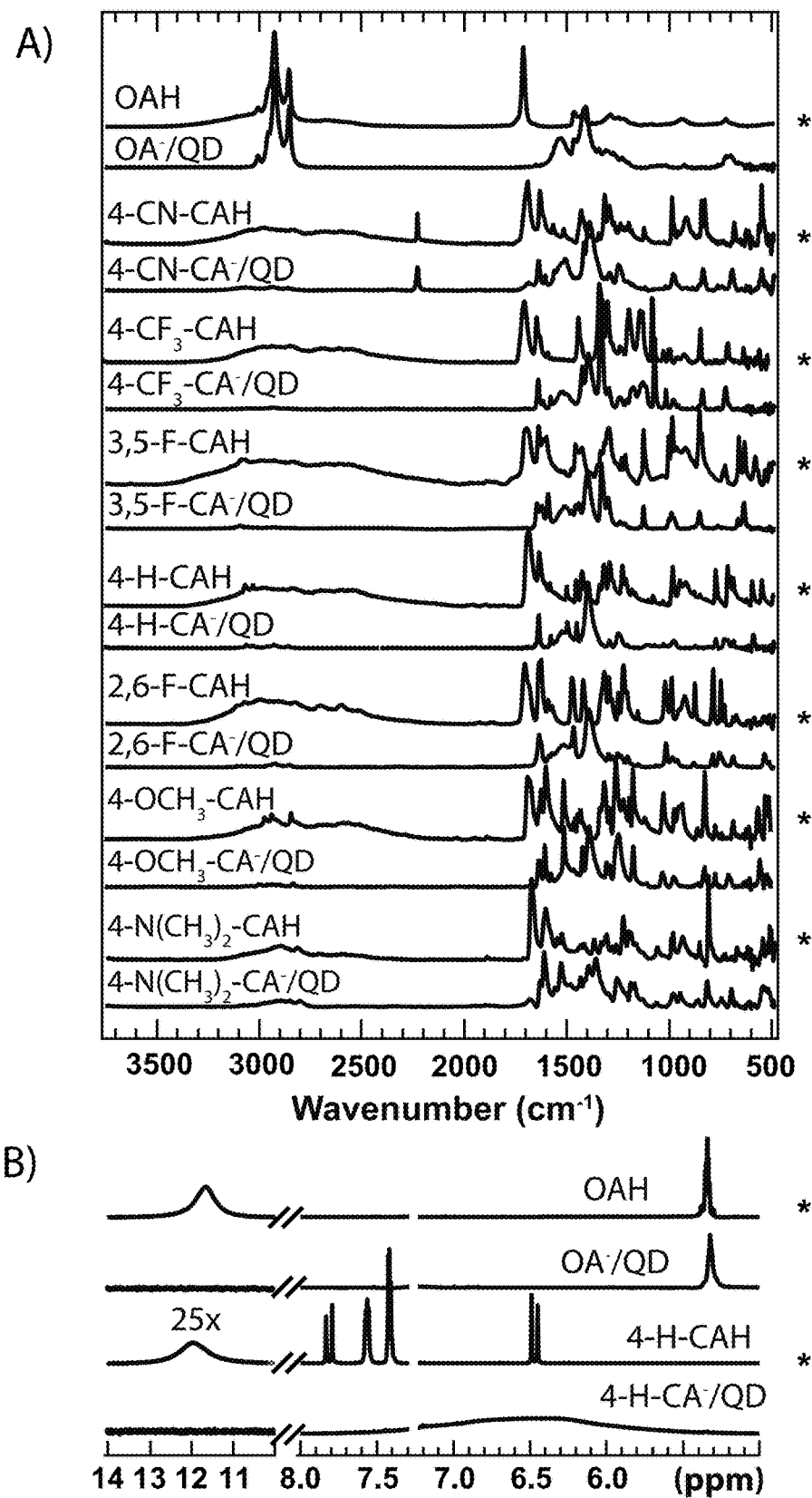
FIG. 10 illustrates surface analysis data of PbS nanocrystals before and after ligand exchange, according to some embodiments of the present disclosure; Panel A FT-IR spectra of neat ligand (asterisks) and ligand/nanocrystal complexes. Panel B $^1$H NMR spectra in $CDCl_3$ of neat ligand (asterisks) and nanocrystals (e.g. ligands coordinated to nanocrystal cores). Both FT-IR and $^1$H NMR analysis suggest the efficient exchange of native $OA^-$ ligands for R-CA$^-$ and removal of excess R-CAH and OAH through precipitation/centrifugation/redissolution purification, according to some embodiments of the present disclosure.

Large-Scale Ligand Exchange Procedure: A robust solution-phase ligand exchange procedure was developed that imparts long-term colloidal stability and from which electronically conductive thin films are readily fabricated using a single-step deposition. Approximately 100 mg of PbS starting nanocrystal core was used, but the procedure should scale so long as concentration ratios are held constant. Each of the eight ligand exchanges were optimized individually due to varying solubility for the pure R-CAHs, as well as the exchanged nanocrystals with R-CA$^-$ termination (see Table 2 below). All of the large-scale ligand exchanges were performed in a nitrogen filled glove box. Exchange occurred upon dropwise addition of a solution of R-CAH exchange ligands, in slight molar excess of that required to reach the absorbance saturation region (see Panels A-H of FIG. 8), to a vigorously stirred dichloromethane solution of PbS OA$^-$/nanocrystal cores with a known concentration. Purification of the fully exchanged PbS nanocrystal cores involved removal of the OAH byproduct and residual R-CAH through multiple cycles of precipitating the exchanged nanocrystals from the exchange solution using a nonpolar antisolvent (hexane), centrifugation, and re-dissolution in the appropriate solvent. All nanocrystals in the original solution were retained in the exchanged solution as determined analytically.

symmetric and asymmetric COO$^-$ stretches at 1530 and 1408 cm$^{-1}$. For each ligand exchange, comparable spectral changes were determined between free R-CAH and nanocrystal core coordinated R-CA$^-$, suggesting that all of the R-CA$^-$ ligands coordinated the nanocrystal core surface in a similar geometry as OA$^-$ and no free R-CAH remained in the samples post purification. Additionally, comparing the OA$^-$/nanocrystal core complex to the R-CA$^-$/nanocrystal core spectra illustrates a drastic decrease in the alkane/alkene C—H stretches around 3000 cm$^{-1}$, indicating efficient displacement of OA$^-$ starting ligand and subsequent removal of OAH. Comparing the $^1$H NMR spectra of free ligand (Panel B of FIG. 10, asterisks) and ligand/nanocrystal core complex after purification (Panel B FIG. 10) illustrates distinct differences. The vinyl peak at 5.3 ppm is significantly broadened for the OA$^-$/nanocrystal core complex and shifted upfield due to dipolar coupling effects that arise from slow rotational diffusion of the OA$^-$ nanocrystal core complex. The OA$^-$/nanocrystal core spectrum shows a lack of the broad OAH acidic proton peak around 12 ppm, in agreement with OA$^-$ chemical identity. Pure 4-H-CAH shows a doublet at 6.47 and 7.81 ppm from the alpha and beta vinyl protons, respectively, with a broad peak around 11.8 from the acidic proton. The remaining peaks at 7.56, 7.40, and 7.42 ppm correspond to the ortho, meta, and para aromatic protons, respectively. The 4-H-CA$^-$/nanocrystal core spectrum shows drastically different features than those of the OA$^-$/nanocrystal core complex and pure 4-H-CAH. The 4-H-CA$^-$/nanocrystal core aromatic and vinyl protons shift upfield and significantly broaden accompanied by a loss of the carboxylic acid peak. Finally, the lack of the broad surface bound OA$^-$ vinyl peak suggests there is very little residual OAH or OA$^-$ in the sample after purification. Overall, the combination of FT-IR and $^1$H NMR analysis provide direct evidence for efficient removal of OA$^-$ from the nanocrystal core surface via an exchange with R-CA$^-$.

Design Parameter: Absolute Energy Level Shifts: Films were cast on Au/glass substrates for X-ray photoelectron

TABLE 2

| | Ligand Solvent[1,2] | Antisolvent | Ligand/nanocrystal core Solvent | Film Fab. Solvent |
|---|---|---|---|---|
| 4(CN)$_2$—CAH | 5:1 ACN:IPA | Hexane | N/A[3] | N/A[3] |
| 4CN—CAH | 5:1 ACN:IPA | Hexane | ACN | ACN |
| 4CF$_3$—CAH | Acetone | Hexane | MeOAc | MeOAc |
| 35F—CAH | MeOAc | Hexane | MeOAc | MeOAc |
| 4H—CAH | DCM | Hexane | DCM/HFIP[4] | 10:1:0.01 DCM:DCB:HFIP |
| 26F—CAH | DCM | Hexane | DCM | 10:1 DCM:DCB |
| 4OCH$_3$—CAH | 5:1 ACN:IPA | Hexane | DCM | 10:1 DCM:DCB |
| 4N(CH$_3$)$_2$—CAH | 2:1 IPA:DCM | Hexane | DCM | 10:1 DCM:DCB |

[1]Heating and sonication were sometimes necessary to solubilize ligand.
[2]Addition of neat ligand solvent had no significant effect on nanocrystal absorbance spectrum in 6:1 ratios of DCM:ligand solvent.
[3]Exchanged nanocrystals were unable to be dispersed in solvents/solvent mixtures on hand.
[4]Without HFIP, exchanged nanocrystals are insoluble. We postulate HFIP aids in breaking apart inter-nanocrystal core ligand Pi-Pi interactions.

Figure 11:
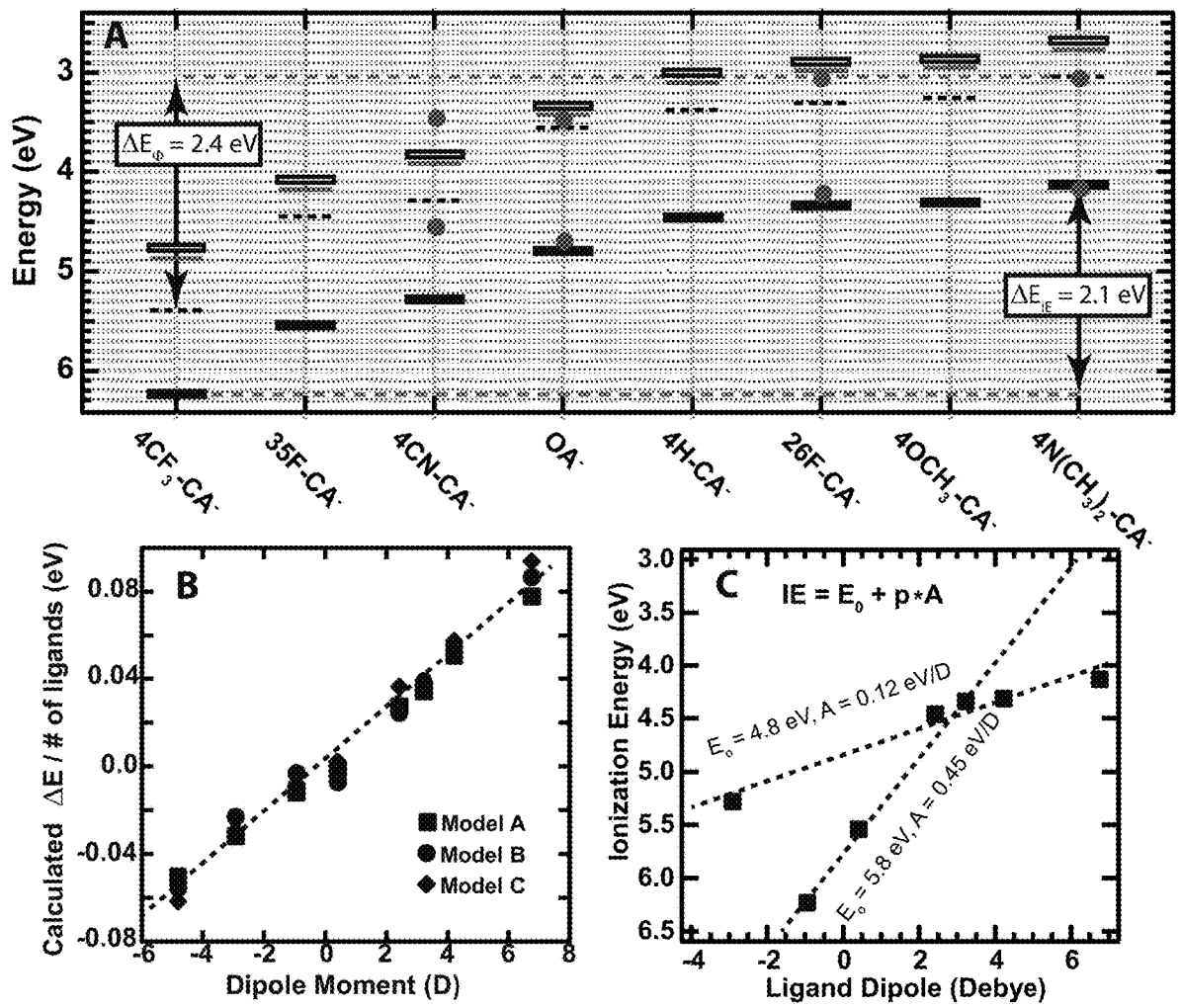
FIG. 11 illustrates energy level shifts of nanocrystals, according to some embodiments of the present disclosure; Panel A XPS measurements of films fabricated from $OA^-$ and R-CA$^-$ terminated 3.2 nm PbS nanocrystal cores; ionization energy (solid rectangles) and work function (dashed black lines). The filled circles are results from CV measurements. Panel B Energy level shifts renormalized by the number of ligands as computed for three different nanocrystal (ligand coordinated with nanocrystal cores) structural models with varying surface coverage as a function of the projected ligand dipole. Panel C Ionization energy vs. projected dipole moment.

The purified ligand exchanged PbS nanocrystal cores were analyzed via FT-IR (Panel A of FIG. 10) and $^1$H NMR (Panel B of FIG. 10) spectroscopy. The FT-IR spectrum of OAH (lighter traces are for the free acid) has a broad —OH feature from 2250-3250 cm$^{-1}$, alkane/alkene C—H stretches around 3000 cm$^{-1}$, and a distinct C=O stretch near 1680 cm$^{-1}$, while for the OA$^-$/nanocrystal core complex (darker traces are ligand/nanocrystal core complexes), the alkane/alkene C—H stretches are retained, but the broad —OH and sharp C=O stretches are no longer present. Evidence of a bidentate carboxylate binding environment is observed with spectroscopy (XPS) measurements. Panel A of FIG. 11 illustrates the experimentally determined $E_{VBM}$ (solid rectangles) and Fermi-level (black dashed) for ligand/nanocrystal core thin films cast via a single deposition step. As a guide, the conduction band minimum ($E_{CBM}$, opaque lines) determined from optical absorbance is provided. Overall, the ionization energy, $E_{VBM}$, is shifted by 2.1 eV accompanied by a work function shift of 2.4 eV. In addition, cyclic voltammetry (CV) was performed on five of the ligand/nanocrystal core colloidal solutions (details below). The CV and XPS data agree reasonably well suggesting that the energy level shifts are indicative of the ligand/nanocrystal core complex and not strictly dependent on nanocrystal thin film characteristics. It is important to note that none of these samples showed significant photocharging during the XPS measurements.

The nanocrystal systems described herein were also investigated computationally. Three different structural models of ligand/nanocrystal core complexes were built having varying surface coverage (see below). Then, using DFT, the energy shift of the nanocrystals was computed by measuring the energy of the HOMO on an absolute energy scale with respect to the vacuum level for each ligand. Panel B) of FIG. 11 shows the relative energy level shifts divided by the number of ligands as a function of the projected dipole moment of the protonated ligands for the three different models. The calculations predict that the energy level shift should be proportional to the ligand dipole, as expected, and proportional to the total number of ligands coordinating the nanocrystal core surface. A simple electrostatic model was parametized from the detailed model. Under the assumption that the nanocrystal core is spherical, and its diameter is larger than the ligand/nanocrystal core interface where the surface dipole layer is present, it can be shown that the energy level shift, $\Delta E$, due the surface dipole layer is proportional to the number of ligands, N, and the effective surface dipole created by an adsorbed ligand, $\tilde{p}$, and inversely proportional to the surface area; $\Delta E \propto N\tilde{p}/r^2$, where r is the nanocrystal core radius. It was assumed that the effective surface dipole $\tilde{p}$, containing both ligand dipole and induced dipole contributions is proportional to the projected ligand dipole p (Table 3). The computed energy level shifts are fit with the equation $E = E_0 + \Delta E = E_0 + A(N/r^2)p$, where $A(N/r^2)$ is allowed to float. Using the experimental nanocrystal core diameter of 3.2 nm (r=1.6 nm) and N=100 ligands, it was determined that $A(N/r^2)$ can vary between 0.26 and 0.36 eV/Debye. The range of experimental dipole moments that were measured was ~10 Debye. The modeling suggests that $\Delta E$ should vary between 2.6 eV and 3.6 eV, which compares favorably with the measured valence band edge (work function) shift of 2.1(2.4) eV.

Figure 12:
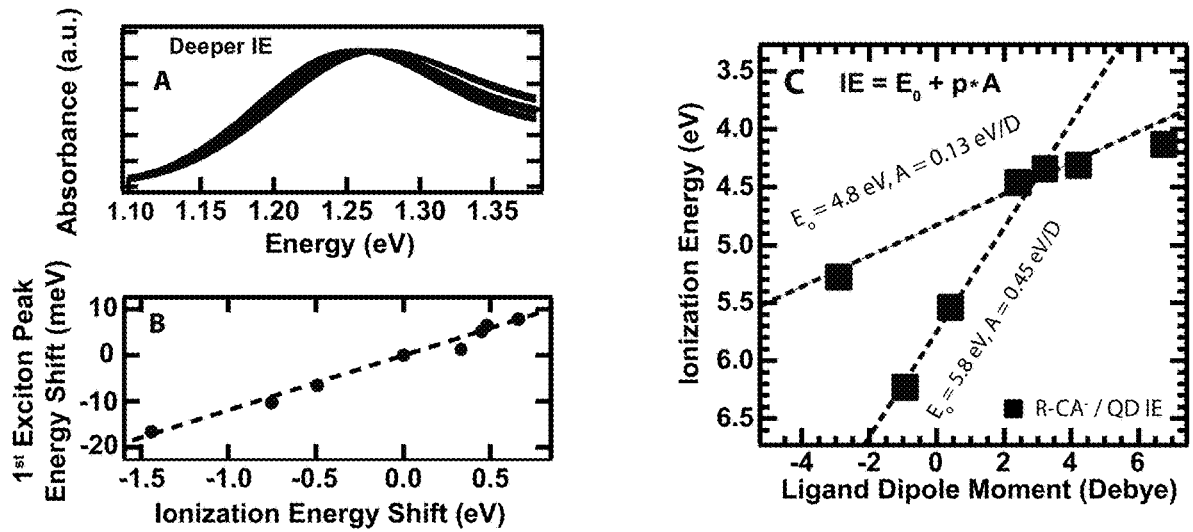
FIG. 12 illustrates in Panel A 1S exciton transition for the nanocrystals, according to some embodiments of the present disclosure. Panel B Shift of 1S exciton transition relative to the $OA^-$/nanocrystal-core as a function of ionization energy (black dashed line is drawn in to highlight linear relationship). Panel C illustrates ionization energies versus ligand dipole moments.
Figure 13:
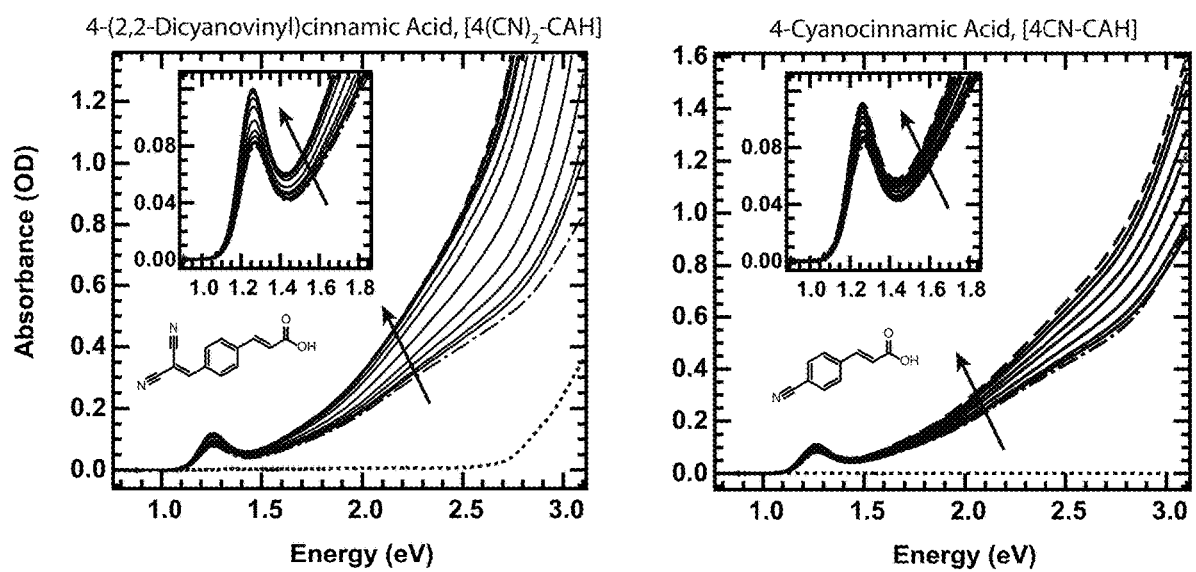
FIGS. 13-16 illustrate quantitative spectrophotometric titration absorbance data for all of the R-CAH ligands, according to some embodiments of the present disclosure. As synthesized (dot dash) and fully exchanged R-CA$^-$ passivated (dashed) PbS nanocrystal cores with intermediate ligand coverages ranging from low to high (solid). The inset shows the first exciton absorbance feature. The lowest lines represent the absorbance spectra of concentrated pure ligand solutions. None of the R-CA$^-$/R-CAH ligands begin absorbing below 2.5 eV.
Figure 14:
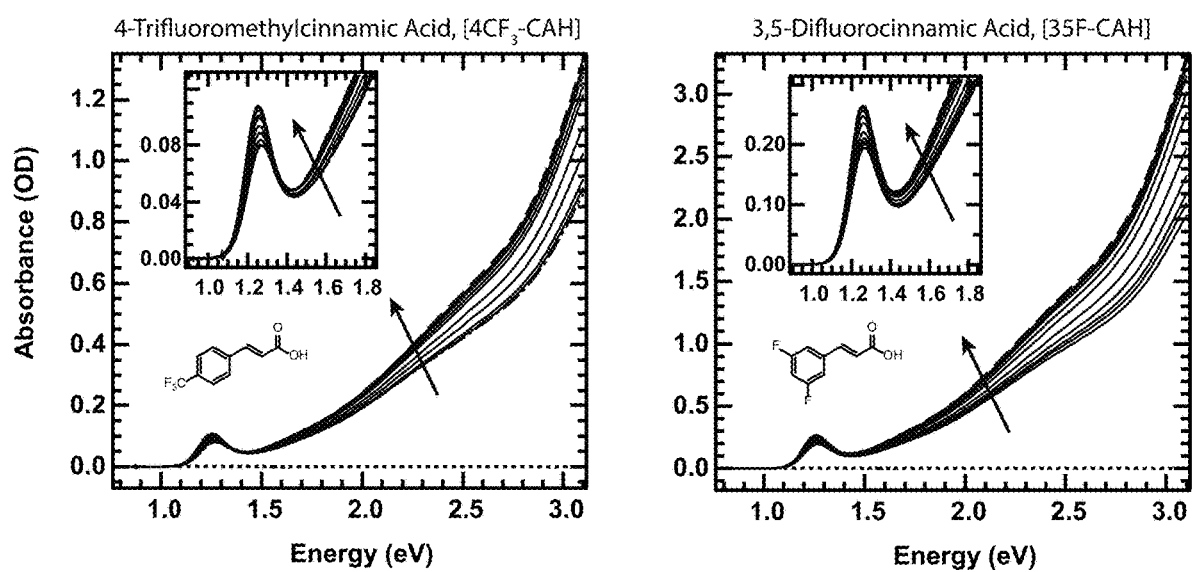
Figure 15:
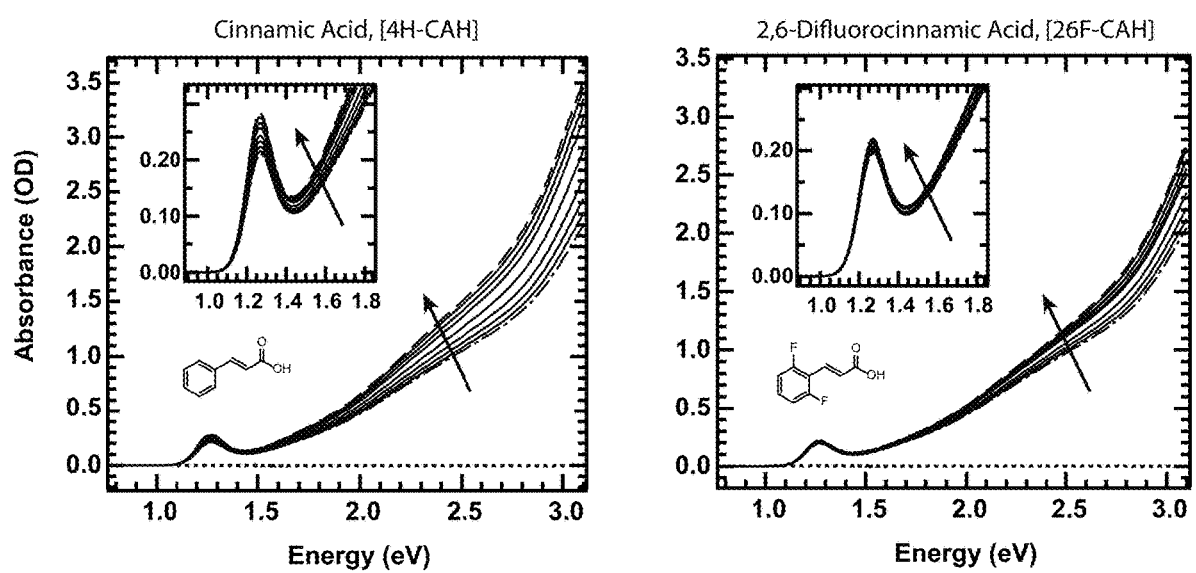
Figure 16:
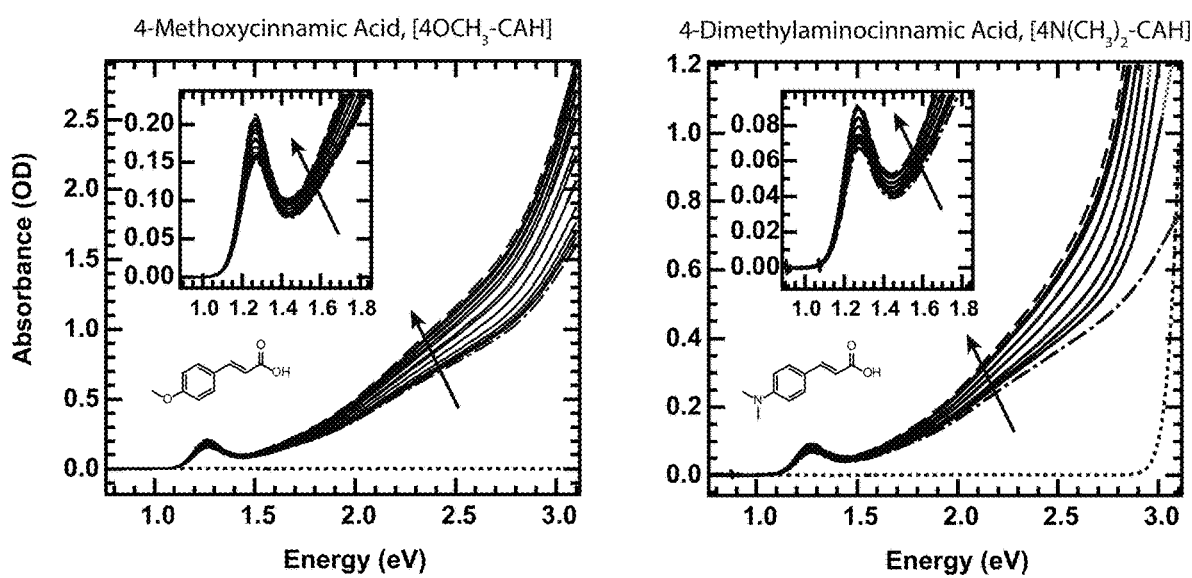

While the total calculated energy level shift compares favorably to the measured data, a different ordering of the ligands was determined to exist between experiment and calculations. In particular, the 4CN-CA$^-$/nanocrystal core complex had the most negative (electron withdrawing) projected dipole, but its measured energy level was not as deep as either the 4CF$_3$-CA$^-$/nanocrystal core or 35F-CA$^-$/nanocrystal core complexes (See Panel B of FIG. 11). A linear least squares fit of the data that only includes the fluorinated ligand/nanocrystal cores finds a best-fit slope of 0.45 eV/Debye (see Panel C of FIG. 11, dashed trace), which is in-line with the upper limit of the calculations. In stark contrast, a best-fit line through the data that excludes the fluorinated ligand/nanocrystal core complexes finds a much shallower slope, 0.12 eV/Debye (see Panel C of FIG. 11, dashed trace), corresponding to about half of the calculated lower limit value, suggesting that the two ligand groups somehow behave differently. Interestingly the 1S exciton peak energy, often a measure of the degree of quantum-confinement, was found to shift in accordance with the ionization energy (Panels A and B FIG. 12). R-CA$^-$ ligands that induce deeper energy level shifts cause the 1S exciton energy to red-shift relative to the OA$^-$/nanocrystal core complex, effectively reducing quantum-confinement and increasing exciton delocalization. Conversely, R-CA$^-$ ligands that induce shallower energy level shifts cause the 1S exciton to blue-shift, increasing quantum-confinement.

The calculated energy levels should be upper estimates based on idealized models. There are at least three reasons why the data and calculations may not agree. (1) The number of ligands on the nanocrystal core surface may not be constant for each ligand. However, this may be discounted because the ligand exchange may be driven to completion, as evidenced by FT-IR and $^1$H NMR analysis and since it is an X-type ligand exchange it must proceed through a proton exchange and is thus 1:1. Furthermore, XPS elemental analysis shows that the C:Pb ratio (See Table 4 below) remains roughly constant for each ligand exchange, suggesting that the ligand-to-nanocrystal core ratio is constant. (2) In the calculation, it may be assumed that ligands are mostly perpendicular to the nanocrystal core surface, which may not always be the case. The binding geometry of the ligands may vary from ligand-to-ligand due to steric or cooperative packing at the nanocrystal core surface. Different ligand binding geometries could induce different projected dipoles than what is calculated here. Finally, (3) there may be ligand/ligand interactions that reduce the effective dipole moment of the 4CN-CA$^-$ ligand or increase the effective dipole of the 4CF$_3$-CA$^-$ and 35F-CA$^-$ ligands. However, possible ligand/ligand interactions that might occur between nanocrystal cores within nanocrystal films may be discounted due to the correspondence of the XPS and CV measurements.

TABLE 3

| | Projected dipoles (Debye) | | HOMO (H), LUMO (L) Quasiparticle Energies (eV) | | | | | | HOMO-LUMO gaps (eV) | | | TDDFT Optical Gaps (eV) | |
|---|---|---|---|---|---|---|---|---|---|---|---|---|---|
| | PBE | SX | PBE H* | PBE L* | GW H | GW L | SX H | SX L | PBE* | SX | GW | PBE | SX |
| 4(CN)$_2$ | −4.81 | −5.04 | −6.59 | −4.31 | −8.26 | −2.27 | −8.81 | −2.66 | 2.28 | 6.15 | 6.00 | 2.64 | 3.76 |
| 4CN | −2.92 | −3.10 | −6.60 | −3.65 | −8.60 | −1.44 | −8.98 | −1.75 | 2.94 | 7.23 | 7.16 | 3.21 | 4.52 |
| 4CF$_3$ | −2.92 | −1.12 | −6.54 | −3.40 | −8.57 | −1.05 | −9.01 | −1.42 | 3.14 | 7.59 | 7.52 | 3.37 | 4.73 |
| 35F | 0.41 | 0.18 | −6.48 | −3.32 | −8.60 | −1.00 | −9.02 | −1.34 | 3.16 | 7.68 | 7.60 | 3.44 | 4.81 |
| 4H | 2.42 | 2.55 | −6.13 | −2.98 | −8.25 | −0.72 | −8.51 | −0.91 | 3.16 | 7.61 | 7.53 | 3.55 | 4.76 |
| 26F | 3.22 | 3.55 | −6.34 | −3.16 | −8.45 | −0.87 | −8.80 | −1.10 | 3.17 | 7.70 | 7.58 | 3.42 | 4.87 |
| 4OCH$_3$ | 4.22 | 3.93 | −5.55 | −2.69 | −7.51 | −0.49 | −7.88 | −0.72 | 2.86 | 7.17 | 7.02 | 3.63 | 4.50 |
| 4N(CH$_3$)$_2$ | 6.76 | 6.26 | −4.91 | −2.42 | −6.66 | −0.34 | −7.07 | −0.55 | 2.49 | 6.52 | 6.32 | 3.24 | 4.11 |

TABLE 4

|  | Pb | S | O | C | F | N | Pb:S | O:Pb | C:Pb |
|---|---|---|---|---|---|---|---|---|---|
| OA$^-$ | 7.01 | 3.10 | 6.91 | 83.05 | ND | ND | 2.26 | 0.99 | 11.85 |
| 4CN-CA$^-$ | 10.71 | 5.54 | 11.37 | 67.05 | ND | 5.33 | 1.93 | 1.06 | 6.26 |
| 4CF$_3$-CA$^-$ | 9.69 | 4.26 | 9.55 | 55.07 | 20.79 | ND | 2.27 | 0.99 | 5.68 |
| 35F-CA$^-$ | 11.28 | 5.24 | 11.31 | 57.49 | 14.68 | ND | 2.15 | 1.00 | 5.10 |
| 4H-CA$^-$ | 12.15 | 5.79 | 13.46 | 68.59 | ND | ND | 2.10 | 1.11 | 5.65 |
| 26F-CA$^-$ | 10.84 | 5.22 | 10.03 | 63.80 | 10.10 | ND | 2.08 | 0.93 | 5.89 |
| 4OCH$_3$-CA$^-$ | 10.05 | 4.44 | 18.86 | 66.36 | ND | ND | 2.12 | 1.88 | 6.60 |
| 4N(CH$_3$)$_2$-CA | 9.63 | 4.73 | 12.07 | 66.26 | ND | 5.39 | 2.04 | 1.25 | 6.88 |

*ND = Not Detected

Each of the nanocrystal films exhibited a Fermi-level indicative of n-type behavior (closer to conduction band) and is consistent with the roughly constant Pb:S ratio measured using XPS (see Table 4). In accordance, the X-type ligand exchange does not involve the removal of surface Pb. Thus, for these ligands, the energy levels are shifted independently of the Fermi-level.

Thus, through a combination of experiment and computational effort, design rules for the enhanced absorbance and absolute energy level shifts observed for a model PbS ligand/nanocrystal core system have been established. It was determined that the ligands with the smallest optical gap will translate into nanocrystals (e.g. nanocrystal core with coordinated ligand) with the highest enhanced absorbance. This theory has been tested for a second class of ligands, benzenethiolates, which has confirmed these design rules (see below). Additionally, it was determined that the magnitude and direction of the observed energy level shifts is proportional to the ligand dipole moment. For ligands with substituted aromatic groups, the Hammett constant can serve as a general guide, but cooperative and packing effects need also be considered. Again, this theory has been tested for benzenthiolate ligands, which confirms the design rule. From this analysis, it is predicted that the energy level shifts for even larger nanocrystal cores should be the same as that measured here regardless of their diameter, since N scales as r$^2$, as long as ligand surface coverage remains about the same. However, the enhanced absorbance depends upon the relative density of nanocrystal core states (DOS) and should decrease for larger nanocrystal cores. The ligand DOS may decrease for larger nanocrystal cores and thus their impact on optical transitions will decrease for larger nanocrystal cores. It is also expected that the established design rules will hold for other organic/inorganic semiconductor nanocrystal systems.

It was determined that ionization energy (work function) of our ligand/nanocrystal core complex library ranges from 6.2 eV (5.4 eV) for the CF$_3$-CA$^-$/nanocrystal core complex to 4.1 eV (3.0 eV) for the 4N(CH$_3$)$_2$-CA$^-$/nanocrystal core complex giving the deepest and shallowest absolute energy levels, respectively, for PbS QDs measured to date. Optoelectronic properties such as enhanced absorbance and absolute energy levels are important design parameters for a large variety of potential solid-state and colloidal nanocrystal applications, such as photovoltaics, LEDs, photoelectrochemical cells, etc. The design principles described herein may allow for nanocrystal system optimization using a-priori engineering approaches.

Additionally, solution-phase ligand exchanges open the door to numerous material processing benefits. Conventional methods to fabricate nanocrystal thin films employ layer-by-layer (LbL), batch-processing fabrication techniques because the ligands most commonly employed do not impart nanocrystal colloidal stability. Methods described herein, however, deposit electronically coupled films via a single deposition step from low boiling point solvents using embodiments of the large-scale ligand exchange procedure described above. Single-step deposition from a colloidal nanocrystal ink allows for high-throughput, roll-to-roll processing where film thickness and morphology can be controlled through nanocrystal concentration and solvent composition. Furthermore, single-step deposition techniques allow for nanocrystal superlattice formation, which holds the potential for highly conductive nanocrystal films through band-like transport. Thus, the flexibility of employing organic ligands to produce functional inorganic/organic systems, as described herein, is very attractive for many emerging applications.

Materials: All chemicals were used as received without further purification unless noted. Anhydrous octane (≥99%), anhydrous diethylene glycol dimethyl ether (diglyme, 99.5%), N,N'-diphenylthiourea (98%), anhydrous toluene (99.5%), anhydrous tetrachloroethylene (TCE, ≥99.9%), anhydrous methyl acetate (MeOAc, 99%), anhydrous 1,2-dichlorobenzene (DCB, 99%), anhydrous hexane (≥99%), anhydrous dichloromethane (DCM, ≥99.8%), anhydrous acetonitrile (ACN, 99.8%), anhydrous isopropanol (IPA, 99.5%), Acetone (≥99.9%, degassed), anhydrous tetrahydrofuran (THF, ≥99.9%), 1,1,1,3,3,3-Hexafluoro-2-propanol (HFIP, ≥99%, degassed), tetrabutylammonium hexafluorophosphate (TBAP, electrochemical grade, ≥99.0%), trans-cinnamic acid (4H-CAH, ≥99%), trans-2,6-difluorocinnamic acid (26F-CAH, 99%), trans-3,5-difluorocinnamic acid (35F-CAH, 99%), trans-4-(trifluoromethyl)cinnamic acid (4CF$_3$-CAH, 99%), 4-methoxycinnamic acid, predominantly trans (4OCH$_3$-CAH, 99%), and 4-(dimethylamino) cinnamic acid, predominantly trans (4N(CH$_3$)$_2$-CAH, 99%), triethylamine (TEA, ≥99%), benzenethiol (4H—SH, ≥98%), 4-aminobenzenethiol (4NH$_2$—SH, 97%), and 4-methylbenzenethiol (4CH$_3$—SH, 98%), 4-bromobenzaldehyde (99%), 4-bromobenzonitrile (99%), anhydrous acrylic acid (99%), N,N-dicyclohexylmethylamine (97%), anhydrous magnesium sulfate(MgSO$_4$), and malononitrile (≥99) were obtained from Sigma Aldrich. 4-(trifluoromethyl)benzenethiol (4CF$_3$—SH, 97%) was obtained from Alfa Aesar. Bis(tri-tert-butylphosphine)palladium (98%) was obtained from Strem Chemicals. Hydrochloric acid (HCl, ACS) was obtained from Macron Fine Chemicals.

Oleat Capped PbS nanocrystal core synthesis: Oleate capped PbS nanocrystal cores with a core diameter of 3.2 nm were synthesized as follows. First, hydroxide-free Pb(oleate)$_2$ was prepared and purified. In a nitrogen glove box, 8.81 g Pb(oleate)$_2$ and 150 mL anhydrous octane were added to a 2-neck 250 mL Schlenk flask equipped with a magnetic stirbar and sealed using a glass stopcock and two rubber septa. Separately, 1.74 g of N,N'-diphenylthiourea and 5 mL of diglyme were mixed in a 20 mL scintillation vial and sealed with a rubber septa. After transferring to a Schlenk line, both vessels were brought to 95° C. in an oil bath under nitrogen and allowed to stir for approximately 30 minutes or until both solutions were clear. Subsequently, the N,N'-diphenylthiourea diglyme solution was quickly injected into the Pb(oleate)₂ octane solution under vigorous stirring. After 60 seconds, the flask now containing a dark brown solution was removed from the oil bath and allowed to cool to room temperature. The septa were then removed under positive nitrogen pressure and replaced with glass stoppers so the volatiles could be removed from the flask under vacuum. The flask was transferred to a nitrogen filled glovebox and the sticky, brown reaction crude was dispersed in approximately 40 mL toluene and split between four 50 mL centrifuge tubes and centrifuged at 7000 RPM for 10 minutes. The brown nanocrystal solution was decanted into four new centrifuge tubes and the remaining dark pellets were discarded. To each centrifuge tube, approximately 30 mL of methyl acetate was added to precipitate the nanocrystals and then centrifuged at 7000 RPM for 10 minutes. This cycle of precipitation and redissolution using toluene and methyl acetate was repeated a total of three times. The nanocrystal product was dried under vacuum and finally suspended in hexane for storage in a nitrogen-filled glove box.

Functionalized Cinnamic Acid Synthesis:

General synthesis: A 20 mL Biotage microwave reaction vial equipped with a teflon magnetic stirbar was charged with aromatic bromide (10 mmol), acrylic acid (11 mmol), N,N-dicyclohexylmethylamine (11 mmol), bis(tri-tert-butyl-phosphine)palladium (1.0 mol %) and THF (10 mL). The vial was capped and the mixture irradiated with a ceiling temperature of 180° C. for 15 minutes. The crude product was then extracted three times with 200 mL dichloromethane and 200 mL acidic aqueous (5% vol HCl) solution. The organic layer was dried with MgSO₄ and the solvent removed using a rotary evaporator. The crude product was further purified by recrystallization in ethanol.

Trans-4-formylcinnamic acid precursor:

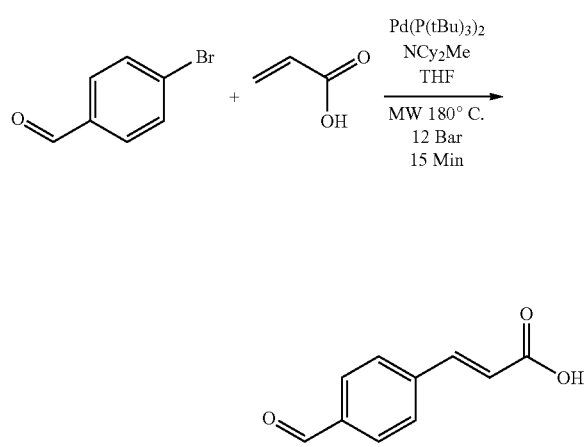

Following the general synthesis procedure from above, the product was obtained after recrystallization from ethanol resulting in a pale yellow powder (72% yield). ¹H NMR (500 MHz, DMSO-d₆) δ 12.59 (s, 1H), 9.98 (s, 1H), 7.88 (s, 4H), 7.62 (d, J=15.6 Hz, 1H), 6.66 (d, J=15.4 Hz, 1H). ¹³C NMR (126 MHz, DMSO-d₆) δ 193.22, 167.80, 142.92, 137.33, 130.42, 129.34, 123.01.

Trans-4-(2,2-dicyanovinyl)cinnamic acid, [4(CN)₂-CAH]:

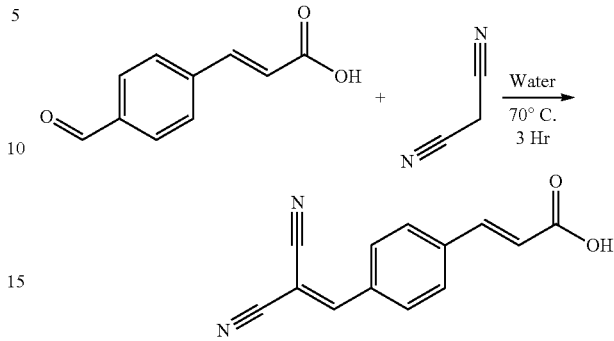

Trans-4-formylcinnamic acid (10 mmol), and malononitrile (10 mmol) were added to 25 mL of distilled water and heated to 70° C. with stirring for 3 hours, then cooled to 0° C. and the solid dark yellow powder precipitate was filtered and air dried (quantitative yield). The product was sufficiently pure after this step to use directly as a ligand for the oleate exchange process. ¹H NMR (500 MHz, DMSO-d₆) δ 12.62 (s, 1H), 8.51 (s, 1H), 7.92 (q, J=10.7, 8.4, 6.1 Hz, 4H), 7.60 (d, J=16.6 Hz, 1H), 6.70 (d, J=16.3 Hz, 1H). ¹³C NMR (126 MHz, DMSO-d₆) δ 167.74, 160.93, 142.60, 140.21, 132.90, 131.48, 129.56, 123.33, 114.76, 113.80, 82.47.

Trans-4-cyanocinnamic acid, [4CN-CAH]:

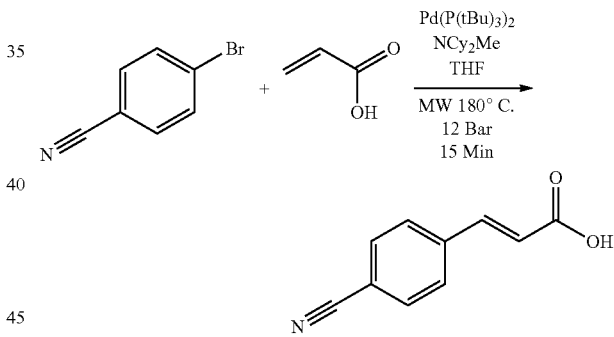

Reaction conditions were similar to the trans-4-formylcinnamic acid synthesis. The product was purified by recrystallization from ethanol affording white needle like crystals (92% yield). The product was sufficiently pure after this step to use directly as a ligand for the oleate exchange process. ¹H NMR (500 MHz, DMSO-d₆) δ 12.63 (s, 1H), 7.89-7.81 (m, 4H), 7.60 (d, J=15.9 Hz, 1H), 6.67 (d, J=15.9 Hz, 1H). ¹³C NMR (126 MHz, DMSO-d₆) δ 167.70, 142.46, 139.35, 133.25, 123.34, 119.15, 112.61.

Large-scale ligand exchange: In a nitrogen-filled glovebox, a nanocrystal DCM solution was prepared and its concentration determined using absorbance spectroscopy. The amount of ligand necessary to completely exchange the standardized nanocrystal solution was determined using the ligand titration absorbance saturation point as a guide (approximately 800-900 ligands per nanocrystal core). In a 20 mL scintillation vial equipped with a magnetic stirbar, the chosen ligand was dissolved in its compatible solvent mixture such that the nanocrystal solution volume:ligand solution volume was 6:1-10:1. The ligand solution was added dropwise to the nanocrystal solution with vigorous stirring, and the exchange was allowed to proceed for approximately 10 minutes. The exchanged nanocrystals were isolated from byproducts (OAH) and excess R-CAH via multiple precipitation, centrifugation, and redissolution cycles (isolation parameters for specific ligands detailed in Table 2 above).

Thin film fabrication: PbS nanocrystal core/ligand thin films were fabricated via a single deposition step using spin-coating. In a nitrogen filled glovebox, PbS nanocrystal core/ligand solutions at concentrations of approximately 200 mg/mL in the solvents indicated in Table 2 were prepared. The solutions were dispensed onto cleaned substrates through a 0.2 μm PTFE syringe filter to remove any aggregated particles and spun at 1500 RPM for 30 seconds. The substrates were finally annealed at 90° C., which produced nanocrystal films that were sufficiently thick that XPS measurements probed outside of the band-bending region of the Au substrate/nanocrystal thin film interface and uniform/devoid of pinholes seeing as Au was not detected during XPS measurements.

Ligand and Ligand/Nanocrystal Core Complex Characterization:

FT-IR Absorbance Measurements: FT-IR absorbance measurements were taken on a Thermo-Nicolet 6700 FT-IR spectrometer in transmission mode with a resolution of 4 cm$^{-1}$. Clean Si plates were used for background measurements, and films of oleate capped nanocrystal cores were drop cast onto the Si plates from hexane. Films of ligand exchanged nanocrystals were cast from solvents detailed in Table 2. Spectra with sloping baselines were baseline-corrected.

Cyclic voltammetry: Cyclic voltammetry (CV) was performed using a CHI 760 D Potentiostat in a three-electrode configuration. Glassy carbon (3 mm diameter), Ag/AgCl (3 M NaCl saturated) and Pt mesh were used as the working electrode, reference electrode, and counter electrode, respectively. After CV measurements, the ferrocene/ferrocenium couple was added as an internal standard. CV measurements of R-CAH ligands were performed in acetone solution under nitrogen protection with a scan rate of 100 mV/s. In order to minimize nanocrystal oxidation, ligand exchanged nanocrystal solutions for CV were prepared in a nitrogen filled glove box. The ligand exchanged PbS nanocrystal cores (~20 mg) were added into the cell containing 20 ml of 0.1 mM TBAP solvent, premixed with TBAP (100 mM solution). Further, the samples were taken from the glove box and measured under nitrogen atmosphere. The net concentration of nanocrystals was maintained at ~1 mg·mL$^{-1}$ for all of the experiments. All potentials were calibrated to a reference potential, either normal hydrogen electrode or vacuum level, as illustrated in Panel A of FIG. 11.

R-CA−/nanocrystal core Complex Cyclic Voltammetry: It was not possible to assign reduction waves (cathodic peaks) and oxidation waves (anodic peaks) for the R-CA−/nanocrystal core solution samples. For the 4N(CH$_3$)$_2$-CA−/nanocrystal core sample, an additional cathodic peak at −0.8 V was observed (not shown). This reduction wave is likely a result of residual OA−/OAH or inter-band trap states. Under anodic scanning potentials, especially between 0.5 V and 1.3 V, the nanocrystals can be adsorbed to the electrode surface (not shown). With adsorbed nanocrystals, we observe changes to the generated peak intensity and shifting of peak positions with subsequent CV scans. This effect complicates the results of CV measurements for solution-phase nanocrystal samples, which influences the cathodic peak formation, such as in the CV scan of the 4CF$_3$-CA− /nanocrystal core sample (not shown). For this reason, fresh nanocrystal samples were made and the electrodes polished for each reported CV scan.

Figure 19:
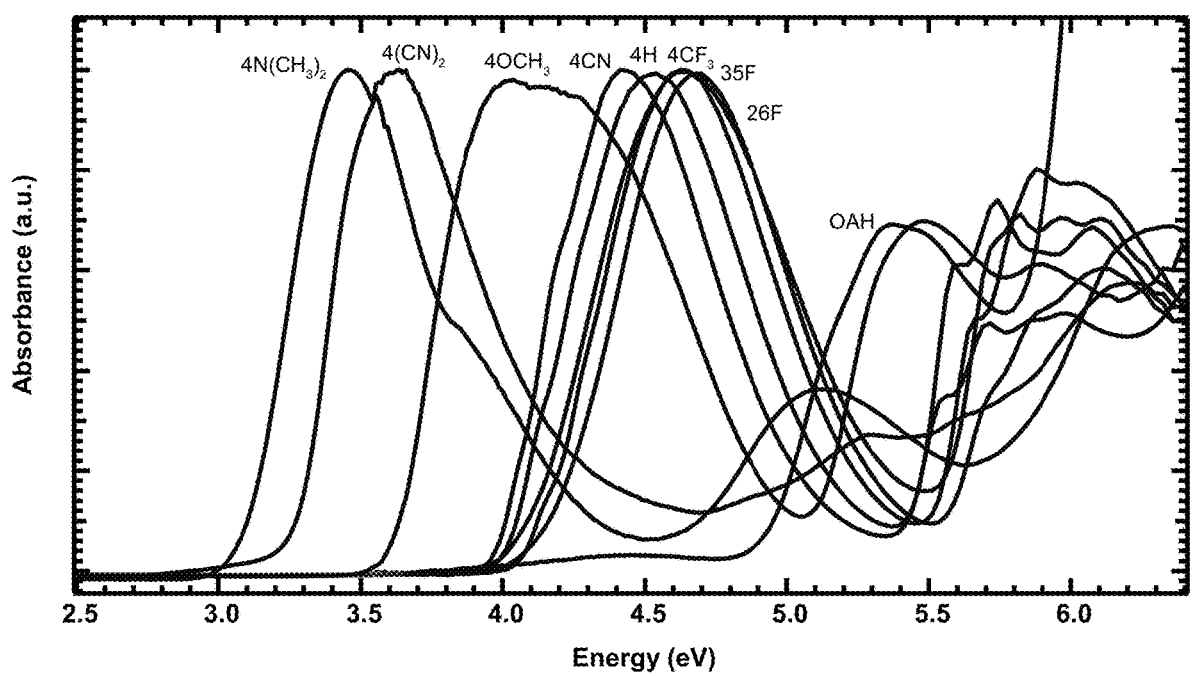
FIG. 19 illustrates absorbance spectra of pure ligands in ethanol normalized at the first absorbance peak feature. The absorbance onset for all of the ligands studied here is greater than 2.5 eV, which means that the absorbance enhancement for the ligand exchanged PbS nanocrystal cores is due to R-CA$^-$/PbS nanocrystal core interactions rather than absorbance from the pure ligand.

Ligand absorbance measurement: Optical absorbance spectra were collected using a Cary 500 UV-Vis-NIR spectrometer (see FIG. 19). Ligand optical gaps were approximated at half the value of the first absorbance feature.

Quantitative $^1$H NMR: $^1$H NMR spectra were recorded on a Bruker Avance III 400 MHz instrument and acquired with sufficiently long delay to allow complete relaxation between pulses (30 seconds). (See FIG. 18.)

Quantitative Spectrophotometric Titration with R-CAHs: Optical absorbance spectra were collected using a Cary 500 UV-Vis-NIR spectrometer. A stock solution of 5-15 μM PbS nanocrystal cores in DCM, standardized from absorbance measurements taken in TCE, was prepared under ambient conditions. Separately, a stock ligand solution was prepared by dissolving a known amount of the ligand in a compatible solvent (see Table 2). The stock ligand solution was combined with neat ligand solvent in separate vials to make diluted ligand samples of varying ligand concentration. In a 2 mm path length cuvette, 0.1 mL of a diluted ligand solution was added to a 0.6 mL of the stock nanocrystal solution to always maintain a constant sample volume of 0.7 mL. The sample was thoroughly mixed, and an absorbance spectrum was immediately taken. This protocol was followed for diluted ligand samples with ligand content ranging from 0-1000 ligands per nanocrystal core per addition. Solution measurement and mixing was performed with calibrated micropipettes. (See FIGS. 13-17.)

XPS measurements: XPS measurements were performed on a Physical Electronics, Inc. 5600 ESCA instrument. Briefly, the radiation is produced by a monochromatic Al (Kα) source centered at 1486.6 eV. The valence band spectra were taken with a step size of 0.05 eV and a pass energy of 5.85 eV. The electron binding energy scale was calibrated using the Fermi edge of cleaned metallic substrates (Au, Mo, Cu, and/or Ag), giving the spectra an uncertainty of ±0.05 eV.

The valence band maximum with respect to Fermi energy ($E_F-E_{VBM}$) is not a simple extraction from the rise in photoelectron intensity (($E_F-E_{onset}$) is the intersection of the linear extraction of the rise in intensity and the baseline). Due to a low density of states at the valence band maximum, a correction to the extracted onset of photoelectron intensity is needed to determine the ($E_F-E_{VBM}$) value for PbS nanocrystal core films. Briefly, the correction depends on the band gap ($E_g$=optical band gap+exciton binding energy); the correction to the onset of photoelectron intensity is correction=0.382-0.226($E_g$). Meaningful XPS data were extracted from nanocrystal films made from the as-synthesized OA−/PbS nanocrystal cores. XPS surface-sensitive elemental analysis is shown in Table 4 above. Cl from solvent mixtures was not detected, suggesting removal of possible residual solvent through film annealing and exposure to high vacuum.

Computational Methods:

k·p Calculations: Isotropic k·p four-band envelope function formalism calculations for PbS nanocrystal cores were performed and parameterized. Using reported literature values of OA− /nanocrystal core bandgaps versus nanocrystal core diameter, a constant correction factor was applied to the nanocrystal core diameter in the calculations to better model the physical boundary conditions of the nanocrystal core. The k·p energies levels relative to vacuum were approximated using a simple dielectric model and parameterized for PbS nanocrystal cores.

General Considerations for DFT: Calculations were performed using the plane wave basis set code Quantum-ESPRESSO using the PBE parametrization of the generalized gradient approximation exchange-correlation functional, optimized norm-conserving pseudopotentials, and a wavefunction cutoff of 80 and 60 Ry for structural relaxations and single point calculations, respectively. Absolute single particle energies were computed with respect to the vacuum level, by determining the average electrostatic potential at the cell boundary and again by applying Makov-Payne-like corrections.

Functionalized Cinnamic Acid Ligands: The functionalized cinnamic acid ligands were optimized in the trans conformation i.e., the acidic proton bound on either one of the carboxylic oxygen atoms. A manual search was performed for locating local minima on the potential energy surface of the functionalized ligand whenever rotatable bonds were found. The observables were computed as a Boltzmann average. The ligand dipole moment was calculated as projected on the molecular axis. It is known that dipole moments converge slowly as a function of the volume of the cell, so additional tests performed additional tests to verify the convergence of the results. It was determined that the calculated ligand dipoles are proportional to their corresponding Hammett constants.

Vertical vacuum electron affinities (EA) and ionization potentials (IP) of the isolated ligands were calculated using dielectric dependent hybrid SX functional and also by performing $G_0W_0$ calculations with PBE starting point. The optical gap of the ligands was computed using adiabatic time-dependent density functional theory as implemented in the Quantum-ESPRESSO with both PBE and the SX functional in the kernel.

Functionalized R-CA-Capped PbS nanocrystal core Models: Charge neutral nanocrystal models were built with Pb excess and by satisfying charge orbital balance: the formal charge of the PbS nanocrystal core was balanced by the formal and opposite charge of the R-CA$^-$ ligands bound on the surface of the nanocrystal core. The method started by cutting out isolated cubes from bulk PbS. Cubes with an odd number of layers were always off-stoichiometric while cubes with even number of layers were always stoichiometric. Three structural models were generated with varying amount of ligands. For model A with formula [Pb$_{43}$S$_{38}$][R-CA$^-$]$_{10}$ a five layer cube was generated and cut off atoms to define a nanocrystal core with small (111) and (110) facets and a near spherical shape. The surface was then passivated with 10 R-CA$^-$ ligands that were bound both on (111) and (100)-like facets. The ligands coordinated the surface Pb atoms in a chelating conformation. Model B was constructed by removing the eight corner atoms of a nanocrystal core with six layers and attaching six R-CA$^-$ ligands to the (100) mini-facets in a bidentate manner and also passivating the corners with iodine atoms to keep charge-orbital balance. The final formula was [Pb$_{62}$S$_{55}$I$_8$][R-CA$^-$]$_6$. Model C was made by removing selected atoms from the PbS core of model B in a way to have larger (111) facets. The surface was then passivated with four R-CA$^-$ ligands while making sure that all the ligands aligned along one cartesian direction. This choice was made for computational reasons: by having ligands point in only one direction, we only had to use larger cell size in one cartesian direction. To ensure charge balance, four iodine atoms were used to passivate the remaining four (111) facets. The formula of model C was [Pb$_{44}$S$_{40}$I$_4$][R-CA$^-$]$_4$. In all three cases several different binding conformations were generated, and it was verified that the models discussed here are the most stable structures.

Figure 20:
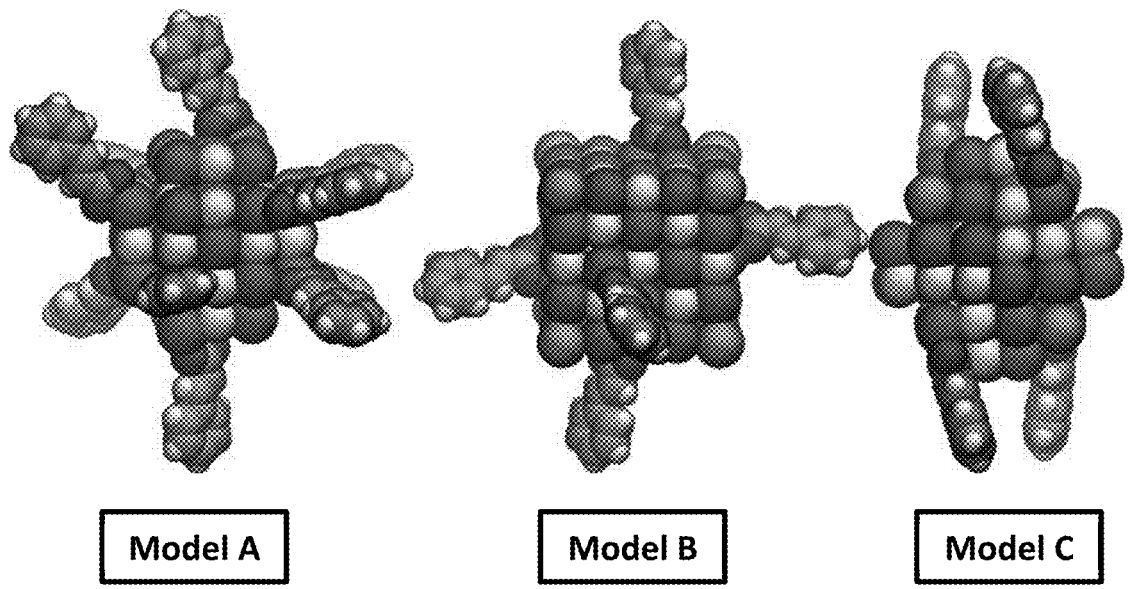
FIG. 20 illustrates ball-and-stick structural models of representative 4H-CA$^-$ capped PbS nanocrystal cores, according to some embodiments of the present disclosure. Red/cyan/white/pink/yellow/tan colors represent oxygen/carbon/hydrogen/iodine/sulfur/lead atoms, respectively.

FIG. 20 shows the ball-and-stick structural model of the relaxed 4H-CA$^-$ covered models. The large variety of these models sampling several possible shapes, facets, and binding moieties allowed us to draw robust conclusions in regards of the band edge position and optical absorption of the ligand/nanocrystal core complexes.

Enhanced optical absorption: The optical absorption of the ligand/nanocrystal core models was computed in the independent particle approximation, which is expected to capture the trends as a function of the aromatic functional group of the ligands. The photoabsorption cross section is proportional to $$\sum_{i \in occ, j \in unocc} \frac{2\omega_{ij}}{3} |\langle \psi_i | r | \psi_j \rangle|^2 \delta(\epsilon - \omega_{ij})$$

where $\omega_{ij}$ is the energy of the transition: $\omega_{ij} = \epsilon_j - \epsilon_i$, and $\langle \psi_i | r | \psi_j \rangle$ is the dipole matrix element between occupied (i) and unoccupied (j) Kohn-Sham wave functions.

Figure 21:
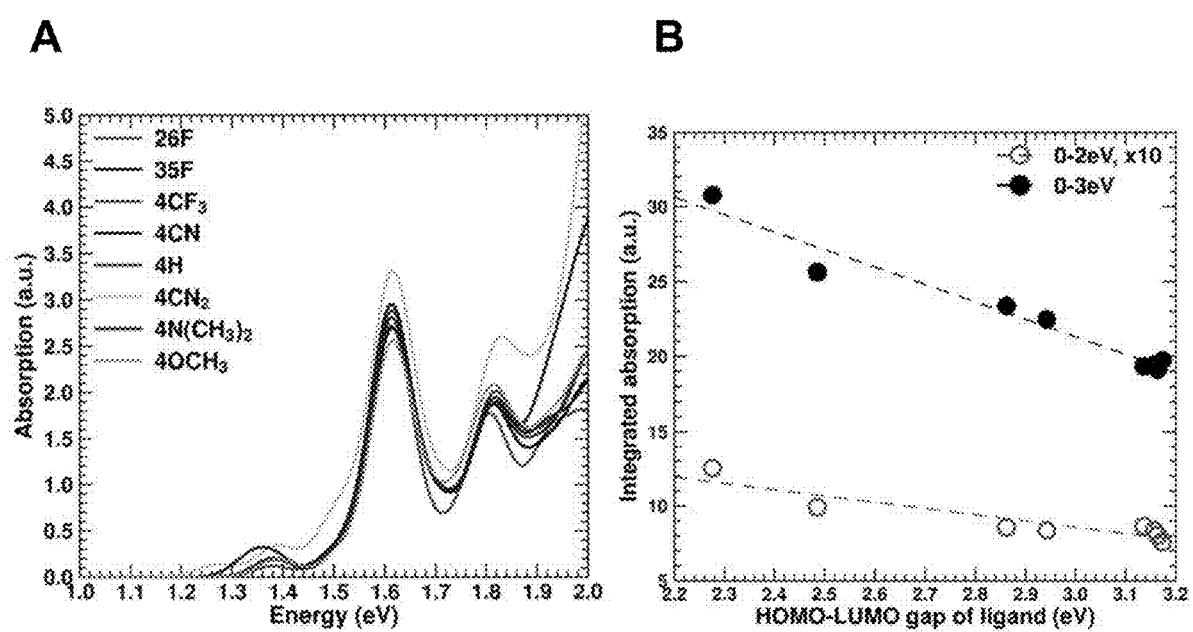
FIG. 21 illustrates (Panel A) optical absorption of ligand/nanocrystal core models C, according to some embodiments of the present disclosure. (Panel B) The integrated absorption of models C as a function of the PBE HOMO-LUMO gap of the ligands, according to some embodiments of the present disclosure. The broadband absorption enhancement shows linear correlation with the ligand optical gap: the smaller the gap, the higher the absorption enhancement.

The optical absorption for all three models was computed, but a detailed study is presented only for model C, as shown in Panel A of FIG. 21. The other two nanocrystal models demonstrated similar absorption characteristics. It was determined that the integrated absorption is inversely proportional to the HOMO-LUMO gap of the isolated protonated ligands (Panel B of FIG. 21). The absorption enhancement observed in our experiments is attributed to optical transitions to/from states that have significant ligand character. This was further corroborated by a detailed joint density of states analysis.

In order to understand the contribution of nanocrystal core and ligand states in the optical absorption, the joint projected density of states were computed. The joint density of states (JDOS) is defined as:

$$JDOS(\epsilon) = \sum_{i \in occ, j \in unocc} \delta(\epsilon - \omega_{ij}) = \int DOS_{occ}(\epsilon' - \epsilon) DOS_{unocc}(\epsilon') d\epsilon'$$

The JDOS is the constant dipole matrix element approximation to the optical absorption and it is a measure of the amount of available optical transitions at given energy, E. The joint projected density of states is the JDOS decomposed into contributions from two spatial regions defined by the nanocrystal core and the ligands (see below for the definitions of $DOS_{QD}$ and $DOS_{ligand}$):

$$JDOS(\epsilon) = \int (DOS_{QD,occ}(\epsilon' - \epsilon) + DOS_{ligand,occ}(\epsilon' - \epsilon))(DOS_{QD,unocc}(\epsilon') + DOS_{ligand,unocc}(\epsilon')) d\epsilon'$$

$$= JDOS_{QD \to QD}(\epsilon) + JDOS_{QD \to ligand}(\epsilon) + JDOS_{ligand \to QD}(\epsilon) + JDOS_{ligand \to ligand}(\epsilon)$$

In addition, it was shown that the JDOS for nanocrystal→nanocrystal transitions stays the same across the ligand library, while the JDOS for the nanocrystal core→ligand and ligand→nanocrystal core transitions change. The relative significance/importance of nanocrystal core→ligand or ligand→nanocrystal core transitions depends on the band alignment between the ligand and the nanocrystal core states while the sum of the two contributions can be controlled by the ligand band gap. Although the JDOS is just an approximation to the absorption spectrum, it was shown that the absorption is most enhanced for ligands, which have the highest nanocrystal core→ligand or ligand→nanocrystal core joint density of states. This provides further evidence that the ligand band gap was the most important factor in determining the enhanced absorbance of the ligand/nanocrystal core complexes.

To further verify the connection between the absorbance enhancement and the ligand band gap, the optical gaps were calculated of the ligands at a higher level of theory using a screened exchange constant (SX) functional. The SX functional is a global hybrid functional, where the mixing fraction $\alpha_{SX}$ is computed by the average screening in the system as the ratio of the screened exchange and exact exchange total energies:

$$\alpha_{SX} = \frac{\sum_{i}^{N} \langle \phi_i | \Sigma_{SEX} | \phi_i \rangle}{\sum_{j}^{N} \langle \phi_j | \Sigma_{EX} | \phi_j \rangle}$$

where N is the number of occupied states in the system, $\phi_i$ is the $i^{th}$ Kohn-Sham state, $\Sigma_{SEX}$ is the screened exchange self energy and $\Sigma_{EX}$ is the exact exchange self energy.

The non-local exchange-correlation potential is then defined as:

$$v_{SX} = \alpha_{SX}\Sigma_{EX} + (1-\alpha_{SX})v_x + v_c$$

In order to compute the optical gaps of the ligands we used adiabatic TDDFT with the SX functional in the kernel (TDSX). There was a good agreement between the computed and measured optical gaps, although TDSX consistently overestimated the gaps by at least 0.1-0.2 eV. This discrepancy might be attributed to solvent effects, since the measurements were done in solvent, while the calculations were performed on ligands in vacuum. Most importantly, however, PBE HOMO-LUMO gaps accurately capture the trend in the gaps as a function of the ligand dipole. Table 3 contains all the computed R-CAH HOMO energies, LUMO energies, and band gaps. We note that we also observe in general a good agreement between G0W0@PBE and SX single particle energies and gaps providing further proof that our SX functional gives a reasonable starting point for computing optical gaps.

In order to extrapolate our findings to larger nanocrystal cores, scaling arguments may be used by recalling that the number of ligand states is proportional to the surface area of the nanocrystal cores and the absorption of nanocrystal cores at higher energies is in general proportional to the nanocrystal core size. Supposing that the ligand coverage stays the same for all nanocrystal core diameters, one can expect that the relative enhanced absorption at higher energies decreases with the inverse of the nanocrystal core diameter. Therefore, the relative absorption enhancement is most important for smaller nanocrystal cores, where multiple exciton generation (MEG) is the most efficient. Also, the absorption enhancement is more pronounced at higher energies, e.g. two times above the gap, the theoretical onset of MEG. This suggests that MEG may be controlled by the ligand dipole as well. The methods provided herein reliably predict and control the position of the ligand states with respect to the nanocrystal core states through modulation of the ligand optical gap.

Band edge shifts: The band edge shift of the nanocrystals was computed by measuring the HOMO and LUMO energy of the ligand/nanocrystal core complexes on an absolute energy scale with respect to the vacuum level as a function of the aromatic functional group of the R-CA⁻ ligands. The HOMO was always localized on the nanocrystal core, with the exception of $4N(CH_3)_2$-CA⁻, where the ligand states were too high in energy relative to the energy of nanocrystal core states, and thus the HOMO was localized on the ligands. Similarly, the LUMO was localized on the nanocrystal core for all cases but $4(CN)_2$-CA⁻, where it was localized on the ligands. In order to disentangle this effect from the ligand dipole induced shift of the nanocrystal core states, a projected density of states analysis was performed and the nanocrystal core HOMO/LUMO as the first state from the band edge that was localized on the nanocrystal core was defined. The projected density of states $DOS_\Omega$ for atoms i belonging to region ZZ is defined as:

$$DOS_\Omega(\epsilon) = \sum_j \sum_{i \in \Omega} |<\varphi_i|\psi_j>|^2 \delta(\epsilon_j - \epsilon),$$

where $\varphi_i$ are atomic orbitals and are Kohn-Sham states with energy $\epsilon_j$. Two regions were defined: one that is comprised of the PbS nanocrystal core ($DOS_{QD}(\epsilon)$) and another one that contains the ligands ($DOS_{ligand}(\epsilon)$).

Figure 22:
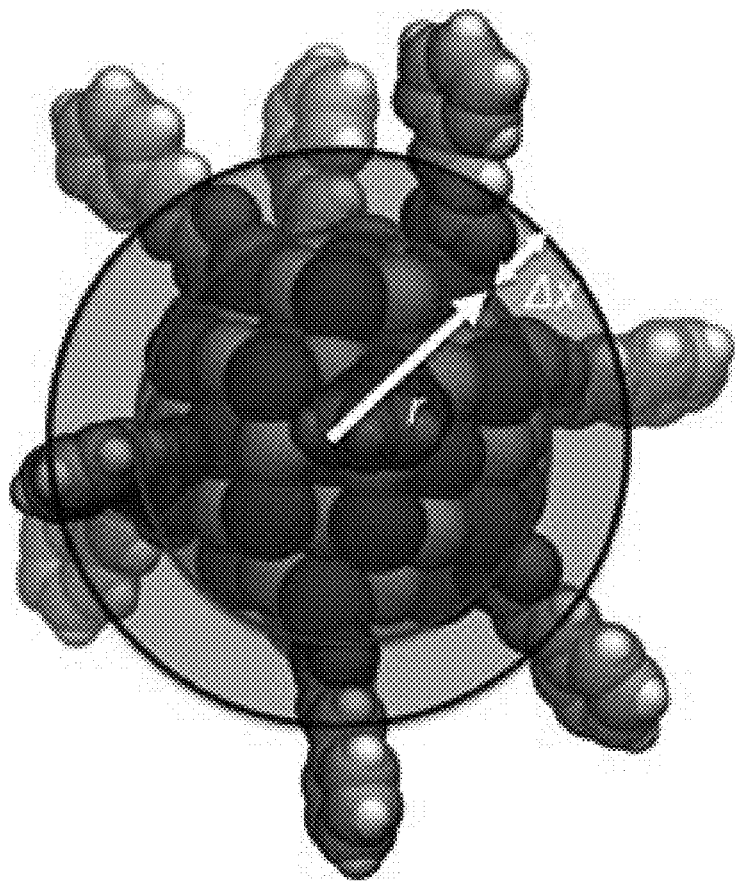
FIG. 22 illustrates a ligand/nanocrystal core model detailing the nanocrystal core diameter, r, and the ligand/nanocrystal core interface where the surface dipole layer is present, Δx, according to some embodiments of the present disclosure.

In order to use the computed band edge shifts for our nanocrystal models to predict the maximum possible band edge shift in the case of experimental conditions, that is, a larger nanocrystal core with more ligands, an electrostatic model was used. The electrostatic model is valid under the assumption that the nanocrystal core is spherical, and its diameter, r, is significantly larger than the ligand/nanocrystal core interface where the surface dipole layer is present, Δx (as depicted in FIG. 22).

Table 5 contains the computed parameters of our electrostatic model. The first column contains the model index. The second column shows the slopes of the lines fitted to a plot of each model's energy (eV) plotted versus their projected dipole (D). The third and fourth columns represent the radius of the nanocrystal cores and the number of surface bound ligands, respectively. The fifth column is the prefactor that incorporates the specific ligand/nanocrystal core interface details. Finally, the last column shows the slope for the experimental conditions.

TABLE 5

|  | AN/r² (eV/D) | r (nm) | N | A | AN/r² (eV/D)* |
| --- | --- | --- | --- | --- | --- |
| Model A | 0.117 | 0.880 | 10 | 0.0091 | 0.355 |
| Model B | 0.067 | 0.765 | 6 | 0.0065 | 0.255 |
| Model C | 0.052 | 0.770 | 4 | 0.0077 | 0.301 |

Comparison with Benzenethiolate (4R—S—) Ligands: In order to test the generality of the design rules established for PbS R-CA⁻/nanocrystal cores, quantitative spectrophotometric titrations and XPS measurements were performed on PbS nanocrystal cores capped with functionalized benzenethiolate (4R—S⁻) ligands. Quantitative spectrophotometric titrations followed a similar procedure as that described for the R-CAHs, except that all of the ligands were dissolved in DCM and included an equimolar amount of TEA to deprotonate the thiol group. Addition of [4CH₃—S⁻][TEA⁺] and [4CF₃—S⁻][TEA⁺] resulted in stable colloidal solutions with ligand equivalents up to 400 at which point addition of more concentrated ligand solutions precipitated the nanocrystals from the exchange solution. In the case of [4NH$_2$—S$^-$][TEA$^+$], addition of ligand equivalents above 100 resulted in precipitation of the PbS nanocrystal cores; however, addition of pure 4NH$_2$—SH in DCM allowed for stable ligand exchanges at all ligand equivalents studied, which are reported below. One explanation is that 4NH$_2$—SH can more easily undergo proton transfer with OA$^-$ than the other thiols. Another possible explanation is that 4NH$_2$—SH undergoes self-deprotonation to form 4N$^+$H$_3$—S$^-$ in solution to drive the exchange. For all of the 4R—S$^-$ ligands studied here, enhanced PbS nanocrystal core broadband absorbance was observed with increased ligand addition and an eventual absorbance saturation similar to that of the 4R-CAH ligands. Additionally, a gradual red shift of the first exciton feature was observed with increased 4R—S$^-$ ligand addition.

A spectra of the fully exchanged 4R—S$^-$/nanocrystal cores, and of the neat 4R—SH ligands in DCM were measured. Using the Hill isotherm model, the integrated absorbance enhancement data were fitted to determine the maximum absorbance enhancement (fitting parameters can be found in Table 6). For the 4R—SH ligands, the raw absorbance spectra were integrated over a wider range, 0.9 to 3.1 eV, than the R-CAH ligands because the thiolate ligands have a higher energy absorbance onset. Similar to the R-CAH ligand exchanges, the enhanced absorbance saturates well past 100 ligands per PbS nanocrystal core, the number of OA$^-$ ligands on the as-synthesized nanocrystal core, which suggests that the ligand exchanges are governed by an equilibrium between surface bound and free ligand that is driven towards surface bound 4R—S$^-$ by the addition of excess 4R—SH. The maximum absorbance enhancement were plotted for each ligand versus the corresponding ligand absorbance onset/optical gap and determined that, consistent with the R-CAH ligands, the experimental enhanced absorbance of the ligand/nanocrystal core complex was greatest when the absorbance onset/optical gap of the ligands is the lowest. The overall magnitude of the 4R—S$^-$/nanocrystal core absorbance enhancement was greater than that of the R-CA$^-$/nanocrystal core, likely because of stronger state mixing between the ligand S binding group states and nanocrystal core S states compared to the ligand COO$^-$ states.

TABLE 6

| | Hill Isotherm | | |
|---|---|---|---|
| | $(\alpha_{tot}/\alpha_{tot}^0)_{max}$ | $K_H$ | n |
| 4NH$_2$—SH | 2.69 | 134.6 | 2.17 |
| 4CH$_3$—SH | 1.60 | 63.7 | 1.54 |
| 4CF$_3$—SH | 1.54 | 68.53 | 1.39 |

Large-scale solution-phase ligand exchanges were attempted using the same 4R—SH ligands employed for spectrophotometric titration (250 [4CH$_3$—S$^-$][TEA$^+$] and [4CF$_3$—S$^-$][TEA$^+$] equivalents, 500 4NH$_2$—SH equivalents) following similar protocols as for the R-CAH exchanges reported here, however, after a single step of precipitation and centrifugation redissolution of the exchanged 4NH$_2$—S$^-$/nanocrystal core and 4CF$_3$—S$^-$/nanocrystal core complexes in any combination of solvents/solvent mixtures on hand was not possible. It was possible to redissolve and purify 4CH$_3$—S$^-$/nanocrystal core complexes for further characterization, but found minor levels of residual surface-bound OA$^-$ as determined by FT-IR.

Films of the large-scale solution-phase ligand exchanged 4CH$_3$—S$^-$/nanocrystal cores were deposited via a single spin coating deposition step for XPS measurements. Since large-scale solution-phase exchanges using other 4R—SH ligands with varying dipole moments to test our design rule were not achieved, fabrication of films of 4R—S$^-$/nanocrystal cores using a layer-by-layer (LbL) film fabrication technique was also attempted. Electronically conductive films of similar thickness were constructed using sequential spin coating cycles by depositing a thin layer of OA$^-$/nanocrystal cores from octane, soaking the film in a 1 mM [4R—S$^-$][TEA$^+$] ACN solution, and washing the film with neat hexane and ACN. Ligands used for this process included [4CH$_3$—S$^-$][TEA$^+$] and [4H—S$^-$][TEA$^+$].

The assertion that the large-scale solution-phase ligand exchanged 4CH$_3$—S$^-$/nanocrystal core sample has some residual OA$^-$ is further substantiated by surface-sensitive XPS elemental analysis (see Table 7). Compared to the 4CH$_3$—S$^-$/nanocrystal core and 4H—S$^-$/nanocrystal core films fabricated using LbL techniques, the large-scale solution-phase ligand exchanged 4CH$_3$—S$^-$/nanocrystal core sample shows elevated O:Pb and C:Pb ratios, which is consistent with excess OA$^-$. Also, N is not detected in the sample, eliminating the possibility that the elevated C:Pb ratio could be from residual TEA$^+$.

In regards to band edge energy shifts, a similar trend was identified for the 4R—S$^-$ terminated nanocrystal cores as for the R-CA$^-$ terminated nanocrystal cores, specifically, the observed band edges shift closer to vacuum with increasing (more positive) ligand dipole moment. In fact, the agreement between the measured ionization energies versus ligand dipole for both classes of ligands (excluding 4CF$_3$-CA$^-$/nanocrystal core and 35F-CA$^-$/nanocrystal core film data) is remarkable, which suggests that the ligand binding group/nanocrystal core surface interface dipole is similar for the carboxylate and thiolate binding groups. Furthermore, a plot was made of IE versus calculated 4R—S$^-$ dipole data from a separate data using a similar PbS 4R—S$^-$/nanocrystal core sample. Again, there is good agreement between the data even though they used slightly different techniques to measure nanocrystal film IE (ambient PES) and to calculate ligand dipoles. The data suggest that the fluorinated ligands form their own unique data set. Overall, the design rule that the ligand dipole affects band edge energy shifts appears to be valid for both classes of ligands discussed herein.

TABLE 7

| | Ligand Dipole (Debye) | Pb | S | O | C | N | Pb:S | O:Pb | C:Pb |
|---|---|---|---|---|---|---|---|---|---|
| 4H—S$^-$ (LbL) | 0.67 | 22.37 | 19.54 | 0.35 | 57.74 | ND | 1.14 | 0.02 | 2.58 |
| 4CH$_3$—S$^-$ (Sln) | 1.19 | 16.50 | 14.68 | 2.61 | 66.21 | ND | 1.12 | 0.16 | 4.01 |
| 4CH$_3$—S$^-$ (LbL) | 1.19 | 19.54 | 16.95 | 0.63 | 62.89 | ND | 1.15 | 0.03 | 3.22 |

*ND = Not Detected

FURTHER EXAMPLES

Example 1

A method comprising: adding an exchange ligand to a solution comprising a first solvent, a nanocrystal core, and a starting ligand, wherein: the exchange ligand comprises a functionalized aromatic molecule, the nanocrystal core comprises at least one of a Group II element, a Group III element, a Group IV element, a Group V element, Group VI element, or a noble metal, the starting ligand is coordinated to a surface of the nanocrystal core to form a starting nanocrystal, the exchange ligand replaces at least a portion of the starting ligand coordinated to the surface, and the exchange ligand coordinates to the surface to produce a ligand-exchanged nanocrystal in the solution.

Example 2

The method of Example 1, wherein the solution is maintained at a temperature between 20° C. and 30° C.

Example 3

The method of Example 1, wherein the first solvent comprises at least one of a polar solvent or a non-polar solvent.

Example 4

The method of Example 3, wherein the first solvent comprises at least one of dichloromethane, pentane, cyclohexane, hexane, heptane, octane, toluene, tetrachoroethylene, chloroform, or carbon tetrachloride.

Example 5

The method of Example 1, wherein the solution has a starting concentration of the starting nanocrystal between 5 µM and 1 mM.

Example 6

The method of Example 1, further comprising, before the adding, dissolving the exchange ligand in a second solvent.

Example 7

The method of Example 6, wherein the second solvent comprises at least one of a polar solvent or a non-polar solvent.

Example 8

The method of Example 7, wherein the second solvent comprises at least one toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, or water.

Example 9

The method of Example 1, wherein the exchange ligand and the nanocrystal core are present at a first ratio between 300:1 and 1000:1.

Example 10

The method of Example 1, wherein the first solvent and the second solvent are present at a second ratio between 6:1 and 10:1.

Example 11

The method of Example 1, further comprising after the adding, mixing a third solvent into the solution, such that the mixing results in the precipitating of at least a portion of the ligand-exchanged nanocrystal.

Example 12

The method of Example 11, wherein the third solvent comprises at least one of a polar solvent or a non-polar solvent.

Example 13

The method of Example 12, wherein the third solvent comprises at least one of pentane, cyclohexane, hexane, heptane, octane, toluene, acetone, acetonitrile, methanol, or ethanol.

Example 14

The method of Example 11, further comprising, after the mixing of the third solvent, at least partially separating the precipitated ligand-exchanged nanocrystal from at least one of the first solvent, the second solvent, or the third solvent.

Example 15

The method of Example 14, wherein the separating is by centrifugation.

Example 16

The method of Example 14, further comprising after the separating, adding a fourth solvent to the precipitated ligand-exchanged nanocrystal, such that the mixing forms at least one of a stable solution-phase colloid or a stable ink.

Example 17

The method of Example 16, wherein the fourth solvent comprises at least one toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, or water.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A nanocrystal comprising:
a nanocrystal core comprising lead sulfide; and
a ligand coordinated to a surface of the nanocrystal core, wherein:
the ligand comprises at least one of cinnamic acid (CAH) or a functionalized CAH molecule.

2. The nanocrystal of claim 1, wherein the functionalized CAH molecule comprises at least one of cinnamic acid, 2,3,4,5,6-pentafluorocinnamic acid, 3,5-bis(trifluoromethyl) cinnamic acid, 4-(2,2-dicyanovinyl)cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tertbutylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino)cinnamic acid, or 3,4-(2,5-pyrrolidinedione)cinnamic acid.

3. The nanocrystal of claim 1, wherein the nanocrystal core has an average particle size between 1 nm and 100 nm.

4. The nanocrystal of claim 2, further comprising an optical absorbance enhancement between 1.1 and 2.0.

5. The nanocrystal of claim 4, further comprising an ionization energy between 6.5 eV and 4.0 eV.

6. The nanocrystal of claim 5, further comprising a work function between 5.5 eV and 3.0 eV.

7. The nanocrystal of claim 1, wherein the nanocrystal core comprises at least one of a uniformly mixed alloy type nanocrystal core, a core-shell type nanocrystal core, a dot-in-rod type nanocrystal core, a dot-on-rod type nanocrystal core, or a Janus particle type nanocrystal core.

8. The nanocrystal of claim 1, wherein the ligand is coordinated to the surface by at least one of a covalent bond, an ionic bond, a van der Waals interaction, dipole-dipole interactions, or a hydrogen-bond.

9. The nanocrystal of claim 8, wherein the ligand is coordinated to the surface of the nanocrystal core by an ionic bond.

10. The nanocrystal of claim 1, wherein the functionalized CAH molecule comprises at least one of 2,3,4,5,6-pentafluorocinnamic acid, 3,5-bis(trifluoromethyl)cinnamic acid, 4-(2,2-dicyanovinyl)cinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-iodocinnamic acid, 4-mercaptocinnamic acid, 4-carboxycinnamic acid, 3,5-dimethoxy-4-hydroxycinnamic acid, 4-methylcinnamic acid, 4-ethylcinnamic acid, 4-tertbutylcinnamic acid, 2,6-difluorocinnamic acid, 2,6-difluoro-4-methoxycinnamic acid, 4-aminocinnamic acid, alpha-cyano-4-dimethylaminocinnamic acid, 4-(di-(4-methoxyphenyl)amino)cinnamic acid, or 3,4-(2,5-pyrrolidinedione)cinnamic acid.

11. A mixture comprising:
a nanocrystal comprising a nanocrystal core and a ligand; and
a solvent, wherein:
the nanocrystal core comprises lead sulfide;
the ligand comprises at least one of cinnamic acid (CAH) or a functionalized CAH molecule,
the ligand is coordinated to a surface of the nanocrystal core, and
the solvent, the nanocrystal, and the ligand form at least one of a stable solution-phase colloid or a stable ink.

12. The mixture of claim 11, wherein the solvent comprises at least one of a polar solvent or a non-polar solvent.

13. The mixture of claim 12, wherein the solvent comprises at least one of toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, or water.

14. A method comprising:
adding an exchange ligand to a solution comprising a first solvent, a nanocrystal core, and a starting ligand, wherein:
the exchange ligand comprises at least one of cinnamic acid (CAH) or a functionalized CAH molecule,
the nanocrystal core comprises lead sulfide,
the starting ligand is coordinated to a surface of the nanocrystal core to form a starting nanocrystal,
the exchange ligand replaces at least a portion of the starting ligand coordinated to the surface, and
the exchange ligand coordinates to the surface to produce a ligand-exchanged nanocrystal in the solution.

15. The method of claim 14, wherein the solution is maintained at a temperature between 20° C. and 30° C.

16. The method of claim 14, wherein the first solvent comprises at least one of a polar solvent or a non-polar solvent.

17. The method of claim 16, wherein the first solvent comprises at least one of dichloromethane, pentane, cyclohexane, hexane, heptane, octane, toluene, tetrachoroethylene, chloroform, or carbon tetrachloride.

18. The method of claim of claim 14, wherein the starting ligand comprises at least one of an alkyl carboxylate, an alkyl amine, an alkyl phosphine, an alkyl phosphonate, or an alkyl thiolate.

19. The method of claim 18, wherein the starting ligand is oleate.

* * * * *